United States Patent [19]
DiNinno et al.

[11] Patent Number: 5,006,519
[45] Date of Patent: Apr. 9, 1991

[54] 2-NAPHTHYL-CARBAPENEM ANTIBACTERIAL AGENTS

[75] Inventors: Frank P. DiNinno, Old Bridge; Mark L. Greenlee, Rahway, both of N.J.

[73] Assignee: Merck & Co., Inc., Rahway, N.J.

[21] Appl. No.: 551,707

[22] Filed: Jul. 11, 1990

[51] Int. Cl.$^5$ .................... C07D 487/04; A61K 31/40
[52] U.S. Cl. ..................................... 514/210; 540/302
[58] Field of Search ......................... 514/210; 540/302

[56] References Cited

U.S. PATENT DOCUMENTS 4,962,101 10/1990 DiNinno ............................. 514/210

Primary Examiner—Robert Gerstl
Attorney, Agent, or Firm—Joseph F. DiPrima; William H. Nicholson

[57] ABSTRACT

Carbapenems of the formula

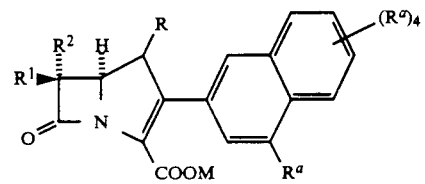

are useful antibacterial agents.

10 Claims, No Drawings

2-NAPHTHYL-CARBAPENEM ANTIBACTERIAL AGENTS

BACKGROUND OF THE INVENTION

The present invention relates to antibacterial agents of the carbapenem class, in which the 2-position sidechain is characterized by a naphthalene moiety, substituted by various neutral substituents, as described in more detail further below.

Thienamycin was an early carbapenem antibacterial agent having a broad spectrum; it has the following formula:

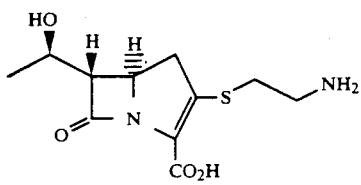

Later, N-formimidoyl thienamycin was discovered; it has the formula:

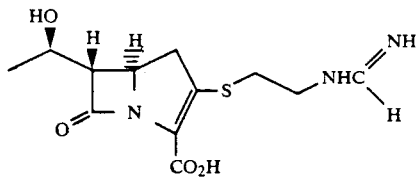

The 2-naphthyl-carbapenems of the present invention are not characterized by a broad antibacterial spectrum such as that of thienamycin or N-formimidoyl thienamycin. Rather, their spectrum of activity is largely limited to gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

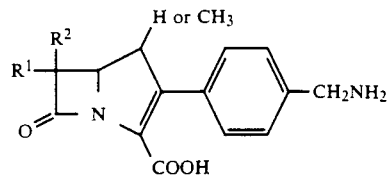

However, there is no description of a substituted naphthyl 2-substituent such as characterizes the compounds of the present invention, nor is there any suggestion of the suprisingly better anti-MRSA/MRCNS activity of the compounds of the present invention.

EP-A-0277 743 describes a particular class of compounds of the formula:

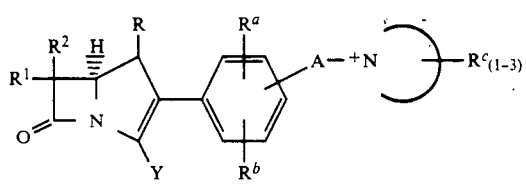

but this limited teaching in no way suggests the totally different compounds of the present invention, nor their surprisingly better anti-MRSA/MRCNS activity.

SUMMARY OF INVENTION

The present invention provides novel carbapenem compounds of the formula:

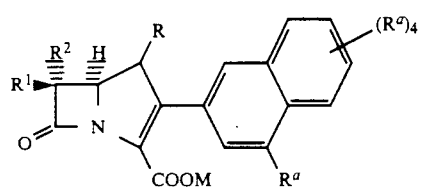

wherein:

R is H or $CH_3$;

$R^1$ and $R^2$ are independently H, $CH_3-$, $CH_3CH_2-$, $(CH_3)_2CH-$, $HOCH_2-$, $CH_3CH(OH)-$, $(CH_3)_2C(OH)-$, $FCH_2CH(OH)-$, $F_2CHCH(OH)-$, $F_3CCH(OH)-$, $CH_3CH(F)-$, $CH_3CF_2-$, or $(CH_3)_2C(F)-$;

$R^a$ are independently selected from the group consisting of hydrogen and the radicals set out below, provided that one to four $R^a$ radicals are other than hydrogen:

(a) a trifluoromethyl group: $-CF_3$;

(b) a halogen atom: $-Br$, $-Cl$, $-F$, or $-I$;

(c) $C_1-C_4$ alkoxy radical: $-OC_{1-4}$ alkyl, wherein the alkyl is optionally mono-substituted by $R^q$, where $R^q$ is a member selected from the group consisting of $-OH$, $-OCH_3$, $-CN$, $-C(O)NH_2$, $-OC(O)NH_2$, $CHO$, $-OC(O)N(CH_3)_2$, $-SO_2NH_2$, $-SO_2N(CH_3)_2$, $-SOCH_3$, $-SO_2CH_3$, $-F$, $-CF_3$, $-COOM^a$ (where $M^a$ is hydrogen, alkali metal, methyl or phenyl), tetrazolyl (where the point of attachment is the carbon atom of the tetrazole ring and one of the nitrogen atoms is monosubstituted by $M^a$ as defined above) and $-SO_3M^b$ (where $M^b$ is hydrogen or an alkali metal);

(d) a hydroxy group: —OH;
(e) a carbonyloxy radical: —O(C=O)$R^s$, where
$R^s$ is $C_{1-4}$ alkyl or phenyl, each of which is optionally mono-substituted by $R^q$ as defined above;
(f) a carbamoyloxy radical: —O(C=O)N($R^y$)$R^z$ where
$R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by —O—, —S—, —S(O)— or —S(O)$_2$—, to form a ring (where the ring is optionally mono-substituted with $R^q$ as defined above);
(g) a sulfur radical: —S(O)$_n$—$R^s$ where n=0-2, and $R^s$ is as defined above;
(h) a sulfamoyl group: —SO$_2$N($R^Y$)$R^z$ where $R^y$ and $R^z$ are as defined above;
(i) azido: N$_3$
(j) a formamido group: —N($R^t$)(C=O)H, where $R^t$ is is H or $C_{1-4}$ alkyl, and the alkyl thereof is optionally mono-substituted by $R^q$ as defined above;
(k) a ($C_1$-$C_4$ alkyl)carbonylamino radical: —N($R^t$)(C=O)$C_{1-4}$ alkyl, where $R^t$ is as defined above, and the alkyl group is also optionally mono-substituted by $R^q$ as defined above;
(l) a ($C_1$-$C_4$ alkoxy)carbonylamino radical: —N($R^t$)(C=O)O$C_{1-4}$ alkyl, where $R^t$ is as defined above, and the alkyl group is also optionally mono-substituted by $R^q$ as defined above;
(m) a ureido group: —N($R^t$)(C=O)N($R^y$)$R^z$ where $R^t$, $R^y$ and $R^z$ are as defined above;
(n) a sulfonamido group: —N($R^t$)SO$_2$ $R^s$, where $R^s$ and $R^t$ are as defined above;
(o) a cyano group: —CN;
(p) a formyl or acetalized formyl radical: —(C=O)H or —CH(OCH$_3$)$_2$;
(q) ($C_1$-$C_4$ alkyl)carbonyl radical wherein the carbonyl is acetalized: —C(OCH$_3$)$_2$$C_{1-4}$ alkyl, where the alkyl is optionally mono-substituted by $R^q$ as define above;
(r) carbonyl radical: —(C=O)$R^s$, where $R^s$ is as defined above;
(s) a hydroximinomethyl radical in which the oxygen or carbon atom is optionally substituted by a $C_1$-$C_4$ alkyl group: —(C=NO$R^z$)$R^y$ where $R^y$ and $R^z$ are as defined above, except they may not be joined together to form a ring;
(t) a ($C_1$-$C_4$ alkoxy)carbonyl radical: —(C=O)O$C_{1-4}$ alkyl, where the alkyl is optionally mono-substituted by $R^q$ as defined above;
(u) a carbamoyl radical: —(C=O)N($R^y$)$R^z$ where $R^y$ and $R^z$ are as defined above;
(v) an N-hydroxycarbamoyl or N($C_1$-$C_4$ alkoxy)-carbamoyl radical in which the nitrogen atom may be additionally substituted by a $C_1$-$C_4$ alkyl group: —(C=O)—N(O$R^y$)$R^z$ where $R^y$ and $R^z$ are as defined above, except they may not be joined together to form a ring;
(w) a thiocarbamoyl group: —(C=S)N($R^y$)(R)$^z$ where $R^y$ and $R^z$ are as defined above;
(x) carboxyl: —COO$M^b$, where $M^b$ is as defined above;
(y) thiocyanate: —SCN;
(z) trifluoromethylthio: —SCF$_3$;
(aa) tetrazolyl, where the point of attachment is the carbon atom of the tetrazole ring and one of the nitrogen atoms is mono-substituted by hydrogen, an alkali metal or a $C_1$-$C_4$ alkyl optionally substituted by $R^q$ as defined above;
(ab) an anionic function selected from the group consisting of: phosphono [P=O(O$M^b$)$_2$]; alkylphosphono {P=O(O$M^b$)-[O($C_1$-$C_4$ alkyl)]}; alkylphosphinyl [P=O(O$M^b$)-($C_1$-$C_4$ alkyl)]; phosphoramido [P=O(O$M^b$)N($R^y$)$R^z$ and P=O-(O$M^b$)NH$R^x$]; sulfino (SO$_2$$M^b$); sulfo (SO$_3$$M^b$); acylsulfonamides selected from the structures CONM$^b$SO$_2$$R^x$, CONM$^b$SO$_2$N($R^y$)$R^z$, SO$_2$NM$^b$CON($R^y$)$R^z$; and SO$_2$NM$^b$CN, where
$R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;
(ac) $C_5$-$C_7$ cycloalkyl group in which one of the carbon atoms in the ring is replaced by a heteroatom selected from O, S, NH or N($C_1$-$C_4$ alkyl) and in which one additional carbon atom may be replaced by NH or N($C_1$-$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;
(ad) $C_2$-$C_4$ alkenyl radical, optionally mono-substituted by one of the substituents (a) to (ac) above and phenyl which is optionally substituted by $R^q$ as defined above;
(ae) $C_2$-$C_4$ alkynyl radical, optionally mono-substituted by one of the substituents (a) to (ac) above;
(af) $C_1$-$C_4$ alkyl radical;
(ag) $C_1$-$C_4$ alkyl mono-substituted by one of the substituents (a)-(ac) above;
(ah) a 2-oxazolidinonyl moiety in which the point of attachment is the nitrogen atom of the oxazolidinone ring, the ring oxygen atom is optionally replaced by a heteroatom selected from S and N$R^t$ (where $R^t$ is as defined above) and one of the saturated carbon atoms of the oxazolidinone ring is optionally mono-substituted by one of the substituents (a) to (ag) above;

M is selected from:
(i) hydrogen;
(ii) a pharmaceutically acceptable esterifying group or removable carboxyl protecting group;
(iii) an alkali metal or other pharmaceutically acceptable cation.

DETAILED DESCRIPTION OF THE INVENTION

The manufacture of compounds of Formula I may be carried out in a three-stage synthesis scheme followed by removal of protecting groups. The objective of the first synthesis stage is to produce a base bromonaphthalene compound which may be converted to the two-position substituent of the carbapenem of Formula I.

The objective of the second synthesis stage is to attach the base naphthalene to the carbapenem. Finally, the objective of the third synthesis stage is to substitute the naphthalene with the desired $R^a$. This third synthesis stage may be performed after the first synthesis stage or during or after the second synthesis stage according to the nature of the various $R^a$.

Flow Sheet A demonstrates a suggested first stage synthesis. Flow Sheets B and C demonstrate two alternative second stage syntheses. The third synthesis varies according to the selected $R^a$.

The first synthesis stage, the synthesis of a substituted bromonaphthalene compound, can be achieved by many processes well-known in the art. The synthesis, substitution, and elaboration of naphthalenes, including bromonaphthalenes, has been thoroughly reviewed in the chemical literature: E. H. Rodd and J. van Alphen in Rodd's Chemistry of Carbon Compounds, Vol. III, Part B, Aromatic Compounds, p. 1253 (1956); N. Campbell in Rodd's Chemistry of Carbon Compounds, 2nd Edition, Vol. III, Part G, Aromatic Compounds, p. 99 (1978); M. J. S. Dewar and P. J. Grisdale, J. Am. Chem. Soc., 84, 3541(1962); W. Adcock and P. R. Wells, Aust. J. Chem., 18, 1351(1965); W. Adcock and M. J. S. Dewar, J. Am. Chem Soc., 89, 386(1967); W. Adcock et al., J. Am. Chem. Soc., 97, 2198(1975); E. A. Dixon et al., Can. J. Chem., 59, 2629(1981). Flow Sheet A below shows a representative starting bromonaphthalene compound, A1.

Employing naphthalene A1, a starting material B1 for the suggested second stage synthesis may be produced. Referring to Flow Sheet A, and starting with A1, it is first necessary to convert the 1-position carboxyl to a desired $R^a$ substituent, or a precursor substituent thereto which is stable to the reaction conditions of adding the naphthalene to a substituted azetidin-2-one precursor of the desired carbapenem. A t-butyldimethylsilyloxymethyl precursor substituent may be obtained on the 1-position of A1 in two steps. Firstly, the carboxyl is reduced to hydroxymethyl by reacting A1 with a reducing agent, such as lithium aluminum hydride (LAH), borane, or the like, in a suitable polar aprotic solvent, such as THF, diethyl ether, or the like, at 0° C. to room temperature (RT). Secondly, the reaction product is isolated and reacted with t-butyldimethylsilyl chloride in dichloromethane with triethylamine and 4-dimethylaminopyridine to produce protected naphthalene B1.

As to the $R^a$ substituent on compound A1, it may be an $R^a$ with or without protecting groups stable to the conditions of producing compound B1 and stable to the conditions of subsequently adding B1 to the carbapenem. Alternatively, it may be a stable precursor substituent which is stable to the conditions of making B1, which is optionally stable to the conditions of adding B1 to the carbapenem and which is convertible to a desired $R^a$ or to another precursor substituent. The identity of the precursor substituent employed is not crucial so long as it does not interfere with synthesis to B1 and so long as it may be thereafter converted to more desireable substitution. Preferred precursor substituents are methyl, hydroxymethyl and protected hydroxymethyl.

With stable $R^a$ or suitable precursor substituents thereof, naphthalene B1 may be added to azetidin-2-one B2 in a Grignard reaction as shown in Flow Sheet B. The Grignard reaction requires that B1 be converted to a Grignard reagent by reaction with magnesium and 1,2-dibromoethane in THF from 20° C. to 60° C. and subsequently contacting B1 as a Grignard reagent with B2 in THF at from −70° C. to about 20° C. to produce azetidin-2-one B3. Alternatively, B1 may be reacted with t-butyllithium, n-butyllithium, or the like in THF at from −78° to −50° C. followed by the addition of magnesium bromide to produce the same Grignard reagent. $R^i$ of B3 is in practice pyrid-2-yl but may clearly be a variety of substituents including aromatic and heteroaromatic substituents. Further $R^i$ might be for example phenyl, pyrimidinyl or thiazolyl.

Azetidin-2-one B3 is an intermediate that may be ring closed to a carbapenem. It is on this intermediate that $R^a$ or precursor substituent such as t-butyldimethylsilyloxymethyl should be modified where such modification is incompatible with the carbapenem nucleus. For example, a convenient reaction to remove the t-butyldimethylsilyl group from the 1-position hydroxymethyl substituent of the naphthalene on compound B3 is to expose compound B3 to a dilute solution of sulfuric acid in methanol at 0° C. Flow Sheet B shows the resulting compound B3A. If the t-butyldimethylsilyl group was removed under the same conditions after cyclization of B3 to a carbapenem, a substantial portion of the carbapenem would be degraded and lost. Thus, modification of the precursor substituent in this instance and replacement with another precursor substituent or even $R^a$ is best performed before closing the carbapenem. Of course it is possible to remove the t-butyldimethylsilyl group in reduced yield after cyclization of B3 to a carbapenem by reaction with tetra-n-butylammonium fluoride and acetic acid in THF.

Compound B3A may be ring closed to carbapenem B4 by refluxing in xylene with a trace of p-hydroquinone for about 1 to 2 hours. It is on this intermediate that final elaboration of $R^a$ from a precursor substituent, e.g. hydroxymethyl, may be accomplished. Removal of the protecting groups then provides the final compound of Formula I. Such final elaboration and deprotection is described in further detail below.

FLOW SHEET A

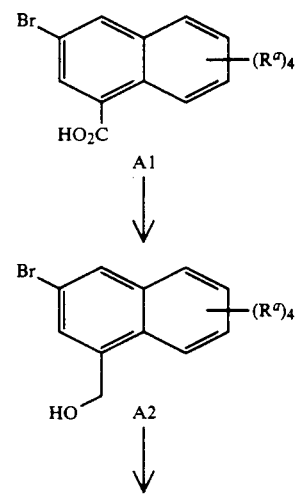

-continued
FLOW SHEET A

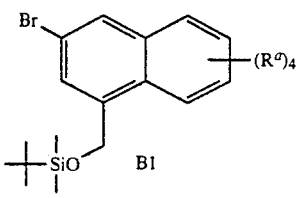
B1

FLOW SHEET B

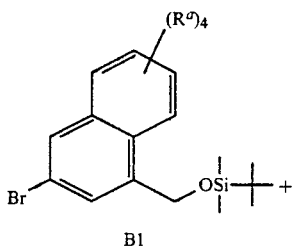
B1

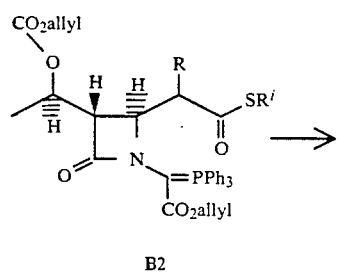
B2

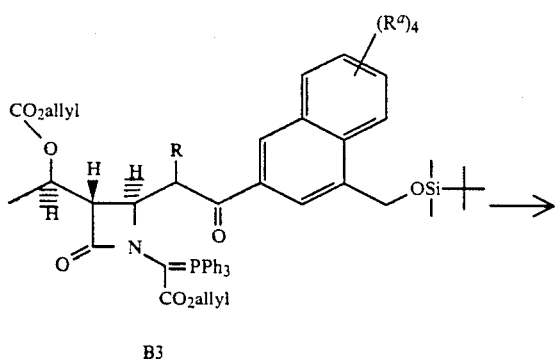
B3

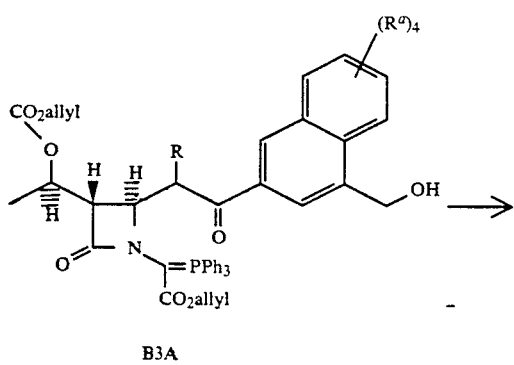
B3A

-continued
FLOW SHEET B

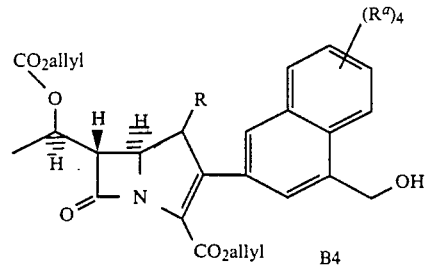
B4

Flow Sheet C shows an alternative second stage synthesis, i.e. attachment of the base naphthalene such as B1 to the 2-position of the carbapenem. This synthesis involves a palladium catalyzed cross-coupling reaction between a carbapenem triflate and a suitably substituted arylstannane, a process which is described in U.S. patent application No. 485,096 filed Feb. 26, 1990, hereby incorporated by reference. In order to apply this synthesis, it is first necessary to modify bromonaphthalene B1 to the trimethylstannylnaphthalene C3. This is accomplished by reacting B1 with t-butyllithium in THF at from −78° to −50° C. followed by the addition of trimethyltin chloride. This provides an intermediate from which the t-butyldimethylsilyl protecting group on the 1-position hydroxymethyl substituent is removed by exposure to tetra-n-butylammonium fluoride in THF yielding C3. Alternatively, bromonaphthalene B1 may be reacted with hexamethylditin in the presence of a palladium(0) catalyst such as tetrakis(triphenylphosphine)palladium in an inert solvent such as toluene at from 25° to 110° C. for from 0.25 to 24 hours to provide, after removal of the t-butyldimethylsilyl protecting group as described above, the same stannane C3. If the t-butyldimethylsilyl group was removed under the same conditions after attachment of the naphthalene side chain to the carbapenem, a much reduced overall yield would be obtained due to degradation of the carbapenem during such removal. Thus modification of the precursor substituent in this instance and replacement with another precursor substituent or even $R^a$ is best performed before attachment to the carbapenem. Referring to Flow Sheet C, the 2-oxocarbapenam C1 is reacted with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in polar aprotic solvent, such as tetrahydrofuran. An organic nitrogen base, such as triethylamine and the like, is then added to the reaction solution followed immediately by a silylating agent, such as trimethylsilyl trifluoromethanesulfonate to provide intermediate C2. An aprotic polar coordinating solvent, such as DMF, 1-methyl-2-pyrrolidinone and the like, is added. This is followed by the addition of a palladium compound, such as tris(dibenzylideneacetone)dipalladium-chloroform, palladium acetate, bis(acetonitrile)palladium(II).chloride and the like, and the stannane C3. Addition of a suitably substituted arylphosphine, such as tris(4-methoxyphenyl)phosphine, tris(2,4,6-trimethoxyphenyl)phosphine and the like, may also be beneficial. A metal halide, such as lithium chloride, zinc chloride and the like, is added and the reaction solution is warmed to a suitable temperature, such as 0° to 50° C., and allowed to stir for a suitable amount of time such as from a few minutes to 48 hours. The carbapenem C4 is obtained by conventional isolation/purification methodology known in the art.

Generally speaking, the milder conditions of the synthesis shown in Flow Sheet C allow for a wider range of functional groups $R^a$ to be present when attaching the naphthalene, than the synthesis illustrated in Flow Sheet B. However, in certain cases it is advantageous for the $R^a$ substituent(s) of the stannane C3 to be introduced in a protected or precursory form. Final elaboration of $R^a$ from a precursor substituent, e.g. hydroxymethyl, may be accomplished on carbapenem intermediate C4. Removal of protecting groups then provides the final compound of Formula I. Such final elaboration and deprotection is described in further detail below.

al. *Tetrahedron*, 39, 2531 (1983); R. N. Guthikonda et al. *J. Med. Chem.*, 30, 871 (1987).

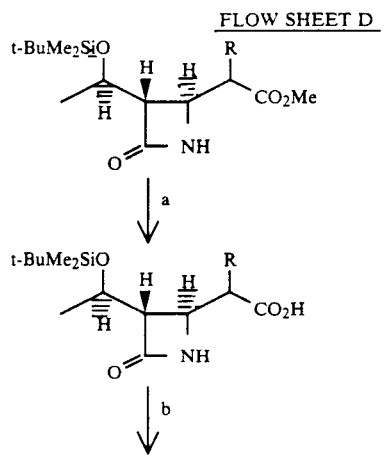

FLOW SHEET D

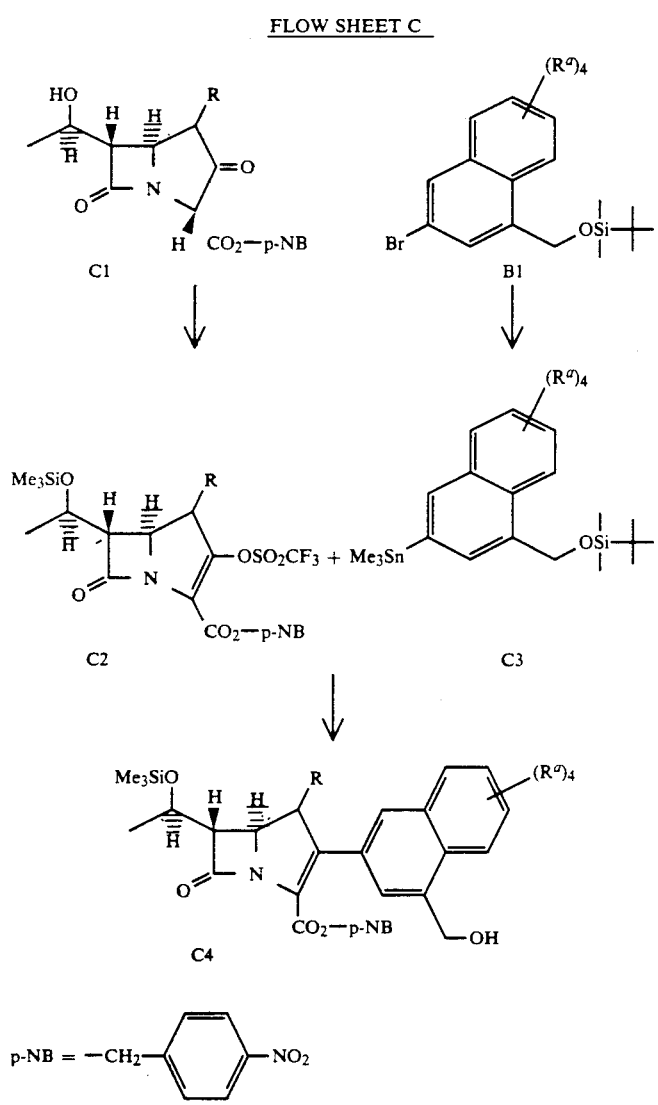

FLOW SHEET C

Azetidin-2-one B2, a pyridyl-thioester, is a well known compound in the production of carbapenems. Diverse synthetic schemes useful to make B2 may be imagined by the skilled artisan. Particularly useful to the instant invention is a synthetic scheme set out further in Flow Sheet D below in which the symbol R is as defined above. The steps for preparing intermediate B2 are analogous to the procedures described, for example, in U.S. Pat. Nos. 4,260,627 and 4,543,257; L. D. Cama et

-continued
FLOW SHEET D

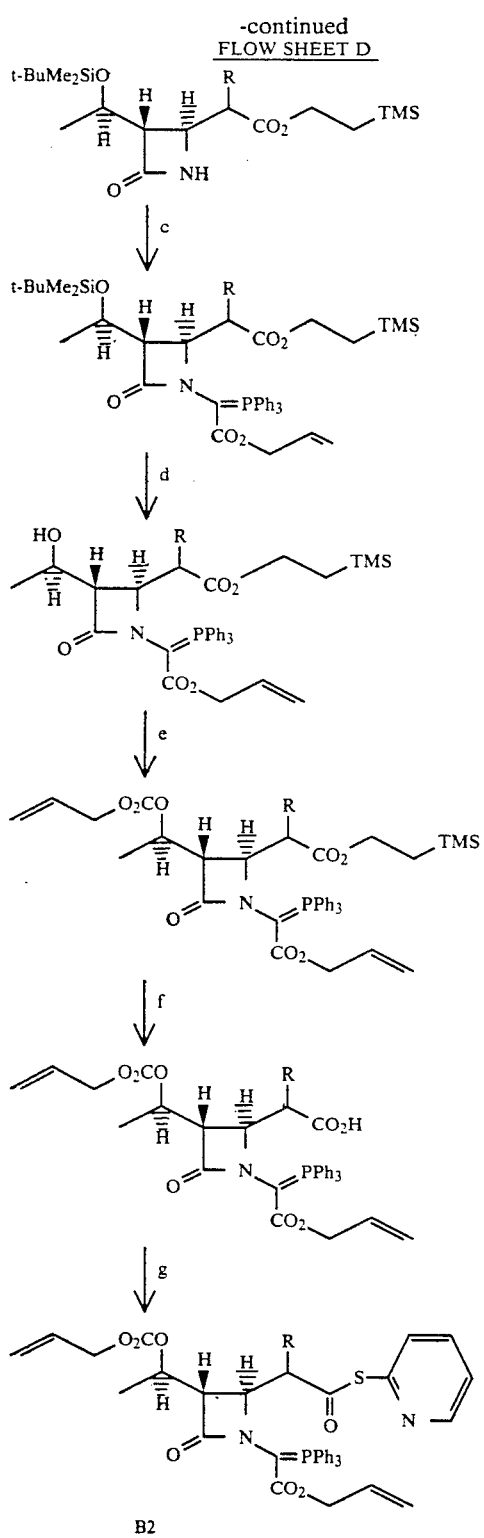

a. NaOH/MeOH b. carbonyl diimidazole/HO〜〜TMS c. i. OHCCO₂〜〜
   ii. SOCl₂
   iii. Ph₃P d. 6N HCl/MeOH

-continued
FLOW SHEET D e. ClCO₂〜〜/DMAP f. nBu₄NF g. Pyr-SS-Pyr./Ph₃P

The steps for preparing the 2-oxocarbapenam intermediate C1 are well known in the art and are explained in ample detail by D. G. Melillo et al., *Tetrahedron Letters*, 21, 2783 (1980), T. Salzmann et al., *J. Am. Chem. Soc.*, 102, 6161 (1980), and L. M. Fuentes, I. Shinkai, and T. N. Salzmann *J. Am. Chem. Soc.*, 108, 4675 (1986). The syntheses are also disclosed in U.S. Pat. No. 4,269,772, U.S. Pat. No. 4,350,631, U.S. Pat. No. 4,383,946 and U.S. Pat. No. 4,414,155 all assigned to Merck and Company, Inc.

The general synthesis description depicted above in the Flow Sheets shows a protected 1-hydroxyethyl substitution on the 6-position of the carbapenem. After final deprotection, a 1-hydroxyethyl substituent is obtained, which is preferred in most cases. However, it has been been found that with certain 2-side-chain selections, the ultimate balance of favorable properties in the overall molecule may be enhanced by selection of the 6-(1-fluoroethyl) moiety instead. Preparation of 6-fluoroalkyl compounds within the scope of the present invention is carried out in a straightforward manner using techniques well known in the art of preparing carbapenem antibacterial compounds. See, e.g., J. G. deVries et al., *Heterocycles*, 23 (8), 1915 (1985); BE 900 718 A (Sandoz) and Japanese Patent Pub. No. 6-0163-882-A (Sanraku Ocean).

The $R^a$ substituents are either neutral or anionic in nature, and are distinguishable from cationic substituents chemically and with respect to the biological properties which they confer. In related compounds, it has been found that the neutral or anionic substituted compounds afford greater water solubility and reduced potential for CNS side effects. Substituents which tend to confer improved water solubility on the overall compound have been found useful, since they are contemplated to thereby improve the transport of the compound involved. Although a substantial number and range of neutral and anionic substituents have been described herein, all of these are contemplated to be a part of the present invention based on the biological performance of substituents related in terms of their medicinal chemistry.

In preferred compounds of Formula I, $R^1$ is hydrogen. More preferably, $R^1$ is hydrogen and $R^2$ is (R)—CH₃CH(OH)— or (R)—CH₃CH(F)—. In the most preferred case, $R^1$ is hydrogen and $R^2$ is (R)—CH₃CH(OH)—. While R=H is usually preferred, there are instances in which R=CH₃ may provide improved chemical stability, water solubility, or pharmacokinetic behavior. The substituent R=CH₃ may be of either configuration, i.e., the α or β-stereoisomer. Additionally, in preferred compounds, at least one $R^a$ in the 1- or 7- position of the naphthalene is other than hydrogen.

Among preferred $R^a$ are $C_{1-4}$ alkyl mono-substituted with hydroxy, such as, hydroxymethyl; formyl; carboxy, such as, —COOK; carbamoyl, such as, —CONH₂; hydroximinomethyl, such as, —CH=NOH or cyano.

In regard to this preferred substitution, the hydroxymethyl may be obtained in any of positions 1, 5, 6, 7 or 8 of the naphthalene ring by employing the appropriately substituted starting material A1 in Flow Sheet A. Thus, proceeding as shown in Flow Sheets A and B, but starting with an "isomeric" A1, a corresponding "isomeric" B3A and a corresponding "isomeric" B4 may be produced.

The preferred formyl substitution on the naphthalene may be obtained from the hydroxymethyl substitution of B4 or isomeric B4 just described by a Swern oxidation. For example, isomeric B4 is oxidized in methylene chloride at from −70° C. to room temperature employing oxalyl chloride-dimethyl sulfoxide, followed by triethylamine, as the active agent. Alternatively, this oxidation may be conveniently accomplished using N-methylmorpholine-N-oxide and a catalytic amount of tetra-n-propyl-ammonium peruthenate in methylene chloride. Obviously, the position of the resultant formyl substitution will depend upon the position of the hydroxymethyl substitution in isomeric B4.

The preferred —CH═NOH substitution on the naphthalene may be conveniently obtained from the formyl substitution just described. This is accomplished simply by exposing the formyl substituted compound to hydroxylamine in an appropriate solvent at room temperature.

The preferred cyano substitution on the naphthalene may be obtained from the —CH═NOH substitution just described. The —CH═NOH substituted compound is dehydrated with triflic anhydride and triethylamine in a solvent at −70° C.

The preferred —COOK substitution on the naphthalene may be obtained from the hydroxymethyl substituted B3A or isomeric B3A described above. For example, an isomeric B3A is oxidized with Jones reagent to convert the hydroxymethyl substituent into a carboxylic acid group. The oxidation with Jones reagent may be incompatible with the carbapenem and thus is optimally performed before ring closure. Prior to ring closure, the carboxy is protected as its allyl ester to permit cyclization of the carbapenem. Protection is carried out by alkylating with allyl bromide and triethylamine. Deprotection following cyclization is carried out with palladium catalyzed deallylation in a solution containing potassium 2-ethylhexanoate as described in McCombie and Jeffrey, *J. Org. Chem.*, 47, 2505 (1983). Deprotection in such a solution yields the desired potassium salt.

The preferred carbamoyl substitution on the naphthalene may be obtained from B3A or "isomeric" B3A by oxidizing the hydroxymethyl with Jones reagent to the corresponding carboxylic acid as described above. This carboxylic acid is converted to —CONH$_2$ by sequentially contacting with 1-ethyl-3-(3-dimethyl-aminopropyl)carbodiimide hydrochloride, 1-hydroxybenzotriazole, and ammonia in an organic solvent at room temperature. Alternatively, the carboxy may be reacted with 1,1'-carbonyldiimidazole in an aprotic polar solvent, such as tetrahydrofuran followed by treatment with aqueous ammonia to give the same —CONH$_2$. Substituted amides may of course be obtained by replacing ammonia with the corresponding substituted amine.

In contrast to the carboxy substitution, this carbamoyl requires no protection for the conditions of carbapenem cyclization.

Compounds substituted with the preferred $R^a$ groups just described may also be obtained by employing the synthesis shown in Flow Sheet C. In this case, the synthetic transformations just described may be carried-out on intermediate C3 prior to attachment of the naphthyl side chain to the carbapenem or on C4 after such attachment.

In the preparation methods described above, the carboxyl group at the 3-position and the hydroxyl group at the 8-position of the carbapenem remain blocked by protecting groups until the final product is prepared. Deblocking may be carried out in a conventional manner. For compounds prepared according to Flow Sheet B, deprotection may be carried out in a palladium catalyzed reaction in a solution containing potassium 2-ethylhexanoate and 2-ethylhexanoic acid or, alternatively, another suitable nucleophile such as pyrrolidine. Alternatively, for those prepared via Flow Sheet C, deprotection is conducted sequentially. Thus, compound C4 is exposed initially to aqueous acidic conditions, acetic acid or dilute HCl or the like, in an organic solvent such as tetrahydrofuran at 0° C. to ambient temperature for from a few minutes to several hours. The resulting desilylated carbapenem may be isolated by conventional techniques, but is more conveniently taken into the final deprotection process. Thus, addition of an inorganic base such as NaHCO$_3$ or KHCO$_3$ and 10% Pd/C followed by hydrogenation provides for the removal of the p-nitrobenzyl protecting group and the formation of the final compound of Formula I.

With reference to the above definitions, "alkyl" means a straight or branched chain aliphatic hydrocarbon radical.

The term "heteroatom" means N, S, or O, selected on an independent basis.

The term "heteroaryl" has been defined herein, in relation to the $R^x$ group, to have a specific and limited meaning, being only monocyclic. It is required that the monocyclic heteroaryl have at least one nitrogen atom, and optionally at most only one additional oxygen or sulfur heteroatom may be present. Heteroaryls of this type are pyrrole and pyridine (one N); and oxazole, thiazole or oxazine (one N+one O or one S). While additional nitrogen atoms may be present together with the first nitrogen and oxygen or sulfur, giving, e.g., a thiadiazole (two N's+one S), the preferred heteroaryls are those where *only* nitrogen hetroatoms are present when there is more than one. Typical of these are pyrazole, imidazole, pyrimidine and pyrazine (two N's) and triazine (three N's).

The heteroaryl group of $R^x$ is always optionally mono-substituted by $R^q$, defined above, and substitution can be on one of the carbon atoms or one of the heteroatoms, although in the latter case certain substitutent choices may not be appropriate.

Listed in Table I are specific compounds of the instant invention. It is understood that $R^2$ substituents which contain a chiral center (ie. —CH(F)CH$_3$ and —CH(OH)CH$_3$) have the (R) configuration in all of the listed compounds:

TABLE 1

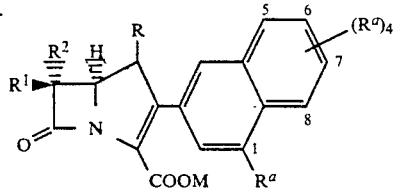

| # | R | R¹ | R² | M | $R^a$ | Ra position |
|---|---|---|---|---|---|---|
| 1 | —H | —H | —CH(F)CH$_3$ | K⁺ | —CN | 1 |
| 2 | —H | —H | —CH(OH)CH$_3$ | K⁺ | —CN | 5 |
| 3 | —H | —H | —CH(OH)CH$_3$ | K⁺ | —CN | 6 |
| 4 | —H | —H | —CH(OH)CH$_3$ | K⁺ | —CN | 7 |
| 5 | —H | —H | —CH(OH)CH$_3$ | K⁺ | —CN | 8 |
| 6 | —H | —H | —CH(OH)CH$_3$ | K⁺ | —OCH$_3$ | 8 |
| 7 | —H | —H | —CH(OH)CH$_3$ | K⁺ | —OCH$_2$CO$_2$Na | 1 |
| 8 | —H | —H | —CH(OH)CH$_3$ | —H | —OCH$_2$CH$_2$OH | 7 |
| 9 | —H | —H | —CH(OH)CH$_3$ | Na⁺ | —CF$_3$ | 1 |
| 10 | —H | —H | —CH(OH)CH$_3$ | Na⁺ | —F | 1 |
| 11 | —H | —H | —CH(OH)CH$_3$ | —H | —Cl | 6 |
| 12 | —H | —H | —CH(OH)CH$_3$ | K⁺ | —Br | 7 |
| 13 | —H | —H | —CH(OH)CH$_3$ | Na⁺ | —F | 1,6,7,8 |
| 14 | —H | —H | —CH(OH)CH$_3$ | K⁺ | —OH | 6,7 |
| 15 | —H | —H | —CH(OH)CH$_3$ | K⁺ | —OCOCH$_3$ | 7 |
| 16 | —H | —H | —CH(OH)CH$_3$ | K⁺ | —OCONH$_2$ | 1 |
| 17 | —H | —H | —CH(OH)CH$_3$ | K⁺ | —SCH$_3$ | 1 |
| 18 | —H | —H | —CH(F)CH$_3$ | K⁺ | —SOCH$_3$ | 7 |
| 19 | —H | —H | —CH(OH)CH$_3$ | Na⁺ | —SO$_2$CH$_3$ | 1 |
| 20 | —H | —H | —CH(OH)CH$_3$ | Na⁺ | —SCH$_2$CH$_2$OH | 1 |
| 21 | —H | —H | —CH(OH)CH$_3$ | K⁺ | —SOCH$_2$CH$_2$OH | 6 |
| 22 | —H | —H | —CH(OH)CH$_3$ | K⁺ | —SCH$_2$CONH$_2$ | 1 |
| 23 | —H | —H | —CH(OH)CH$_3$ | Na⁺ | —SO$_2$NH$_2$ | 1 |
| 24 | —H | —H | —CH(OH)CH$_3$ | Na⁺ | —SO$_2$N(CH$_3$)$_2$ | 1,5 |
| 25 | —H | —H | —CF$_2$CH$_3$ | K⁺ | —NHCHO | 6,8 |
| 26 | —CH$_3$ | —H | —CH(OH)CH$_3$ | K⁺ | —NHCOCH$_3$ | 6,8 |
| 27 | —H | —H | —CH(OH)CH$_3$ | K⁺ | —NHCO$_2$CH$_3$ | 1,6 |
| 28 | —H | —H | —CH(OH)CH$_3$ | K⁺ | —NHSO$_2$CH$_3$ | 1 |
| 29 | —H | —H | —CH(OH)CH$_3$ | K⁺ | —COCH$_3$ | 1 |
| 30 | —H | —H | —CH(OH)CH$_3$ | K⁺ | —COCH$_2$OH | 6 |
| 31 | —H | —H | —CH(OH)CH$_3$ | Na⁺ | —CH=NOCH$_3$ | 6 |
| 32 | —CH$_3$ | —H | —CH(OH)CH$_3$ | Na⁺ | —CH=NOCH$_2$CO$_2$Na | 7 |
| 33 | —H | —H | —CH(OH)CH$_3$ | —H | —CH=NOCMe$_2$CO$_2$H | 1 |
| 34 | —H | —H | —CH(OH)CH$_3$ | K⁺ | —CH=NOCMe$_2$CO$_2$Me | 8 |
| 35 | —H | —H | —CH(OH)CH$_3$ | K⁺ | —CO$_2$CH$_2$CH$_2$OH | 1 |
| 36 | —H | —H | —CH(OH)CH$_3$ | K⁺ | —CONHCH$_3$ | 8 |
| 37 | —H | —H | —CH(OH)CH$_3$ | K⁺ | —CON(CH$_3$)$_2$ | 6 |
| 38 | —H | —H | —CH(OH)CH$_3$ | K⁺ | —CONHCH$_2$CN | 1 |
| 39 | —H | —H | —CH(OH)CH$_3$ | K⁺ | —CONHCH$_2$CONH$_2$ | 1 |
| 40 | —H | —H | —CH(OH)CH$_3$ | K⁺ | —CONHCH$_2$CO$_2$H | 6 |
| 41 | —H | —H | —CH(OH)CH$_3$ | Na⁺ | —CONHOH | 1 |
| 42 | —H | —H | —CH(OH)CH$_3$ | Na⁺ | —CONHOCH$_3$ | 7 |
| 43 | —H | —H | —CH(OH)CH$_3$ | Na⁺ | tetrazolyl | 1 |
| 44 | —H | —H | —CH(OH)CH$_3$ | Na⁺ | —SCF$_3$ | 1 |
| 45 | —H | —H | —CH(OH)CH$_3$ | —H | —PO$_3$NaH | 7 |
| 46 | —H | —H | —CH(OH)CH$_3$ | K⁺ | —CONHSO$_2$Ph | 7 |
| 47 | —H | —H | —CH(OH)CH$_3$ | K⁺ | —CONHSO$_2$NH$_2$ | 1 |
| 48 | —H | —H | —CH(OH)CH$_3$ | Na⁺ | —SO$_3$Na | 7 |
| 49 | —H | —H | —CH(OH)CH$_3$ | Na⁺ | —SO$_2$NHCN | 1 |
| 50 | —H | —H | —CH(F)CH$_3$ | Na⁺ | —SO$_2$NHCONH$_2$ | 1 |
| 51 | —H | —H | —CH(OH)CH$_3$ | K⁺ | —CH=CHCN | 8 |
| 52 | —H | —H | —CH(OH)CH$_3$ | K⁺ | —CH=CHCONH$_2$ | 1 |
| 53 | —H | —H | —CH(F)CH$_3$ | Na⁺ | —CH=CHCO$_2$Na | 7 |
| 54 | —H | —H | —CH(OH)CH$_3$ | Na⁺ | —C≡C—CONH$_2$ | 1 |
| 55 | —CH$_3$ | —H | —CH(OH)CH$_3$ | K⁺ | —C≡C—CN | 1 |
| 56 | —H | —H | —CH$_2$CH$_3$ | K⁺ | —CH$_2$N$_3$ | 8 |
| 57 | —H | —H | —CH(OH)CH$_3$ | Na⁺ | —CH$_2$CO$_2$Na | 7 |
| 58 | —H | —H | —CH$_2$CH$_3$ | K⁺ | —OH | 3 |
| 59 | —H | —H | —CH(OH)CH$_3$ | K⁺ | —CHO | 1 |
| 60 | —H | —H | —CH(OH)CH$_3$ | K⁺ | —CHO | 5 |
| 61 | —H | —H | —CH(OH)CH$_3$ | K⁺ | —CHO | 6 |
| 62 | —H | —H | —CH(OH)CH$_3$ | K⁺ | —CHO | 7 |
| 63 | —H | —H | —CH(OH)CH$_3$ | K⁺ | —CHO | 8 |
| 64 | —H | —H | —CH(OH)CH$_3$ | K⁺ | —CH=NOH | 1 |
| 65 | —H | —H | —CH(OH)CH$_3$ | K⁺ | —CH=NOH | 5 |
| 66 | —H | —H | —CH(OH)CH$_3$ | K⁺ | —CH=NOH | 6 |
| 67 | —H | —H | —CH(OH)CH$_3$ | K⁺ | —CH=NOH | 7 |
| 68 | —H | —H | —CH(OH)CH$_3$ | K⁺ | —CH=NOH | 8 |
| 69 | —H | —H | —CH(OH)CH$_3$ | K⁺ | —CONH$_2$ | 1 |
| 70 | —H | —H | —CH(OH)CH$_3$ | K⁺ | —CONH$_2$ | 5 |

TABLE 1-continued

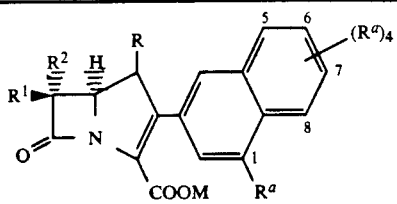

| # | R | R¹ | R² | M | Rᵃ | | |
|---|---|---|---|---|---|---|---|
| 71 | —H | —H | —CH(OH)CH₃ | K⁺ | —CONH₂ | 6 | |
| 72 | —H | —H | —CH(F)CH₃ | K⁺ | —CONH₂ | 7 | |
| 73 | —H | —H | —CH(OH)CH₃ | K⁺ | —CONH₂ | 8 | |
| 74 | —H | —H | —CH(F)CH₃ | Na⁺ | —CO₂Na | 1 | |
| 75 | —H | —H | —CH(OH)CH₃ | Na⁺ | —CO₂Na | 5 | |
| 76 | —H | —H | —CH(OH)CH₃ | Na⁺ | —CO₂Na | 6 | |
| 77 | —H | —H | —CH(F)CH₃ | Na⁺ | —CO₂Na | 7 | |
| 78 | —H | —H | —CH₂OH | Na⁺ | —CO₂Na | 8 | |
| 79 | —H | —H | —CH(OH)CH₃ | K⁺ | —CH₂OH | 8 | |
| 80 | —H | —H | —CH(OH)CH₃ | K⁺ | —CH₂OH | 5 | |
| 81 | —H | —H | —CH(OH)CH₃ | K⁺ | —CH₂OH | 6 | |
| 82 | —H | —H | —CH(OH)CH₃ | K⁺ | —CH₂OH | 7 | |
| 83 | —H | —H | —CH(OH)CH₃ | K⁺ | —CH₂N₃ | 1 | |
| 84 | —H | —H | —CH(OH)CH₃ | K⁺ | —CH₂OCONH₂ | 1 | |
| 85 | —H | —H | —CH(OH)CH₃ | K⁺ | —CN | 1 | |
| 86 | —H | —H | —CH(OH)CH₃ | K⁺ | —(Z)—CH=CHCN | 1 | |
| 87 | —H | —H | —CH(OH)CH₃ | K⁺ | —(E)—CH=CHCN | 1 | |
| 88 | —H | —H | —CH(OH)CH₃ | K⁺ | —CH₂OH | 1 | |
| 89 | —H | —H | —CH(OH)CH₃ | K⁺ | —CONH₂ | 7 | |
| 90 | —H | —H | —CH(OH)CH₃ | K⁺ | —OH | 7 | |
| 91 | —H | —H | —CH(OH)CH₃ | K⁺ | —(Z)—CH=CHCN | 7 | |
| 92 | —H | —H | —CH(OH)CH₃ | K⁺ | —(E)—CH=CHCN | 7 | |
| | | | | | | | Ra' |
| 93 | —H | —H | —CH(OH)CH₃ | K⁺ | 1-F | | 7-CH₂OH |
| 94 | —H | —H | —CH(OH)CH₃ | K⁺ | 1-F | | 7-CHO |
| 95 | —H | —H | —CH(OH)CH₃ | K⁺ | 1-F | | 7-CONH₂ |
| 96 | —H | —H | —CH(OH)CH₃ | K⁺ | 1-SOCH₃ | | 7-CHO |
| 97 | —H | —H | —CH(OH)CH₃ | K⁺ | 1-SOCH₃ | | 8-CHO |
| 98 | —H | —H | —CH(OH)CH₃ | K⁺ | 1-CN | | 7-SOCH₃ |
| 99 | —H | —H | —CH(OH)CH₃ | K⁺ | 1-CONH₂ | | 7-CH₂OH |
| 100 | —H | —H | —CH(OH)CH₃ | K⁺ | 1-CONH₂ | | 8-SOCH₃ |
| 101 | —H | —H | —CH(OH)CH₃ | K⁺ | 1-CN | | 8-CH₂OH |
| 102 | —H | —H | —CH(OH)CH₃ | K⁺ | 7-CHO | | 8-OH |
| 103 | —H | —H | —CH(OH)CH₃ | K⁺ | 1-CONH₂ | | 7-CHO |
| 104 | —H | —H | —CH(OH)CH₃ | K⁺ | 1-CN | | 7-CO₂K |

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Examples of such ester protecting groups include benzhydryl, p-nitrobenzyl, 2-naphthylmethyl, allyl, benzyl, trichloroethyl, silyl such as trimethylsilyl, trimethylsilylethyl, phenacyl, p-methoxybenzyl, acetonyl, o-nitrobenzyl, p-methoxyphenyl, 4-pyridylmethyl, and t-butyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10–60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5–50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5–25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occuring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European patent applications No. 79102616.4 filed July 24, 1979 (Pat. Nos. 0 007 614; and 82107174.3), filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

The invention is further defined by reference to the following examples, which are intended to be illustrative and not limiting. All temperatures are in degrees Celsius.

EXAMPLE 1

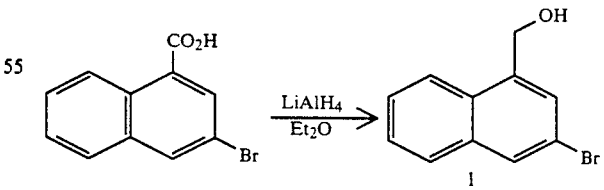

3-Bromo-1-(hydroxymethyl)napthalene (1)

To a stirred solution of 1.0 g (3.98 mmoles) of 3-bromo-1-naphthoic acid in 38 ml of anhydrous diethyl ether was added dropwise a 0.86 M lithium aluminum hydride in diethyl ether solution (44 ml, 3.78 mmoles). The resulting slurry was stirred at reflux under a $N_2$ atmosphere for 3 hours. The slurry was cooled to rt and moist Na₂SO₄ was added. The resulting slurry was filtered through a MgSO₄ plug and the filtrate concentrated under vacuum to provide 782.7 mg of white residue. Purification on silica gel plates which were eluted with CH₂Cl₂ gave 722.3 mg of 3-bromo-1-(hydroxymethyl)naphthalene as a white crystalline solid.

¹H-NMR (300 MHz, CDCl₃): δ 1.79 (br s, CH₂O$\underline{H}$), 5.15 (s, C$\underline{H_2}$OH), 7.54 (m, naphthyl-H6 and H7), 7.66 (s, naphthyl-H2), 7.79 (m, naphthyl-H5), 7.97 (s, naphthyl-H4), 8.03 ppm (m, naphthyl-H8).

IR (CH₂Cl₂): 3605 cm⁻¹.

EXAMPLE 2

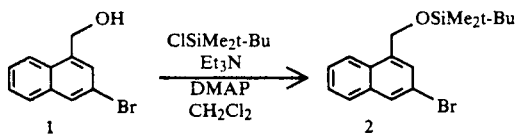

3-Bromo-1-(t-butyldimethylsilyloxymethyl)naphthalene (2)

To a solution of 1.49 g (6.3 mmoles) of 3-bromo-1-(hydroxymethyl)-naphthalene in 25 ml anhydrous CH₂Cl₂ were added sequentially N,N-dimethyl-4-aminopyridine (76.8 mg, 0.63 mmoles), t-butyldimethylchlorosilane (1.23 g, 8.2 mmoles) and triethylamine (1.22 ml, 8.8 mmoles). The resulting solution was stirred at room temperature for 2 hours under a N₂ atmosphere and then partitioned between EtOAc and ice/H₂O. The organic phase was separated, washed with brine, dried with anhydrous Na₂SO₄, filtered and concentrated under vacuum to provide a pale yellow liquid. The crude reaction residue was purified by column chromatography (44 g silica gel, packed and eluted with 9:1 hexanes: CH₂Cl₂) to provide 2.19 g of the title compound as a clear liquid.

¹H-NMR (200 MHz, CDCl₃): δ 0.15 (s, C$\underline{H_3}$Si), 0.97 (s,(C$\underline{H_3}$)₃CSi), 5.17 (s, C$\underline{H_2}$O), 7.22–7.95 ppm (m, ArH).

EXAMPLE 3

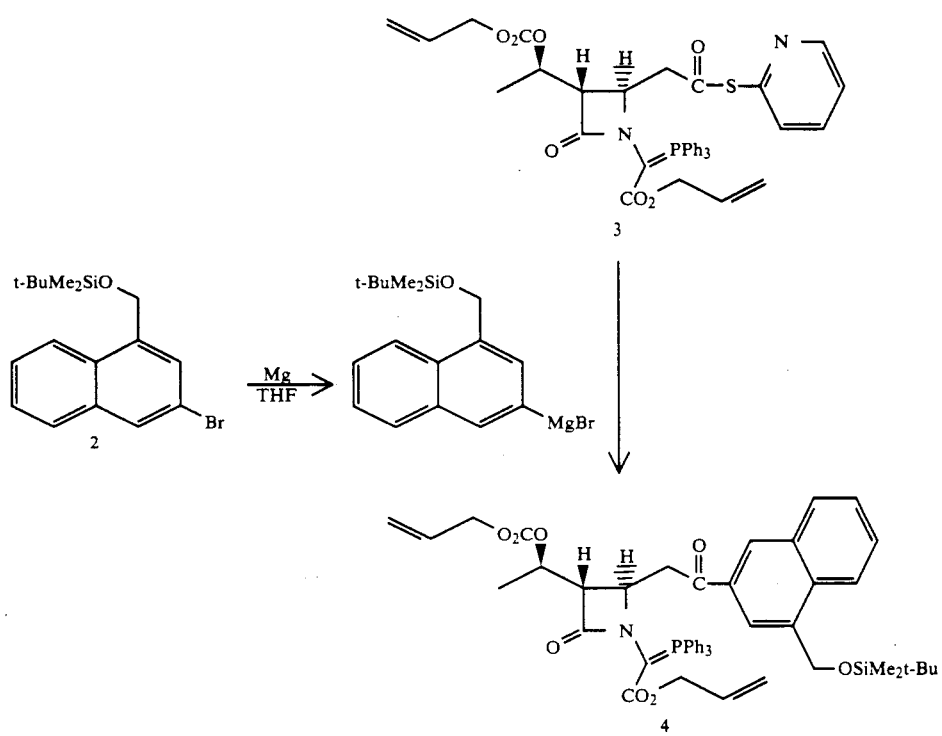

(3S,4R)-1-(Allyloxycarbonyl-triphenylphosphoranylidene)methyl-3-[1R-(allyloxycarbonyloxy)ethyl]-4-[1-(t-butyldimethylsilyloxymethyl)-3-naphthylcarbonyl]methyl-azetidin-2-one (4)

To a mixture of magnesium turnings (160 mg, 6.6 mmoles) in 15 ml anhydrous THF was added the bromo-naphthalene 2 prepared in the previous example (2.09 g, 6.0 mmoles). The stirring was stopped and 0.035 ml of 1,2-dibromoethane was added close to the magnesium surface. Heat was applied to initiate the reaction and the mixture then stirred at 30° under a N₂ atmosphere for 2.5 hours. At the end of this time the heat was removed and the yellow Grignard solution was employed as described below.

To a solution of 2.11 g (3.0 mmoles) of (3S,4R)-1-(allyloxycarbonyltriphenylphosphorylidene)methyl-3-[1R-(allyloxycarbonyloxy)ethyl]-4-[(2-pyridylthio)carbonyl]methyl-azetidin-2-one, 3 , in 20 ml anhydrous tetrahydrofuran at −9° under a N₂ atmosphere was added 11.5 ml (ca. 4.6 mmoles) of the above Grignard solution. The reaction solution was stirred at −9° under a N₂ atmosphere for 50 minutes and then 10 ml of saturated aqueous ammonium chloride solution was added. The resulting mixture was partitioned between EtOAc and ice/H₂O. The organic phase was separated and washed twice with ice/5 N aqueous NaOH solution. The organic phase was then washed with brine, dried with anhydrous Na₂SO₄, filtered and concentrated under vacuum to provide 3.09 g of a yellow foam. The crude reaction residue was purified by column chromatography (150 g silica gel; packed and eluted with 3:2; hexanes: EtOAc) to provide 2.24 g of the title compound as a pale yellow foam.

¹H-NMR (300 MHz, CDCl₃): inter alia δ 0.15 (s, CH₃Si), 0.96 (s, (CH₃)₃CSi), 1.18 (d, J=6.9 Hz, CH₃CHCH), 5.18 ppm (s, naphthyl-CH₂).

IR (CH₂Cl₂): 1745, 1680, 1615 cm⁻¹.

EXAMPLE 4

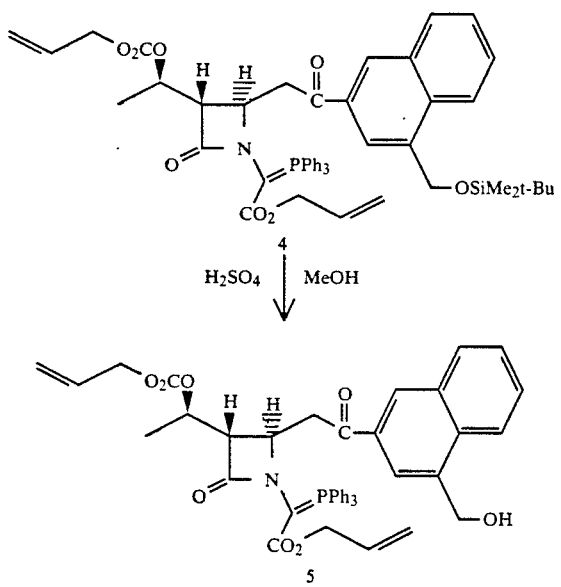

(3S,4R)-1-(Allyloxycarbonyltriphenylphosphoranylidene)methyl-3-[1R-(allyloxycarbonyloxy)ethyl]-4[1-(hydroxymethyl)-3-naphthylcarbonyl]-methyl-azetidin-2-one (5)

To a solution of 2.9 g (3.32 mmoles) of azetidinone 4 in 35 ml anhydrous MeOH at 0° under a N₂ atmosphere was added a 0.75 M methanolic sulfuric acid solution (6.64 ml, 4.98 mmoles). The resulting solution was stirred 1.5 hrs at 0° and then was concentrated under vacuum to 15 ml volume. The solution was then partitioned between EtOAc and ice/H₂O/saturated aqueous bicarbonate. The organic phase was separated and washed with brine, dried with anhydrous Na₂SO₄, filtered and concentrated under vacuum to provide 2.50 g of the title compound as a yellow foam.

¹H-NMR (300 MHz, CDCl₃): inter alia δ 1.17 ppm (d, J=6.8 Hz, CH₃CHCH).

IR (CH₂Cl₂): 3600,1745,1680,1620, cm⁻¹.

EXAMPLE 5

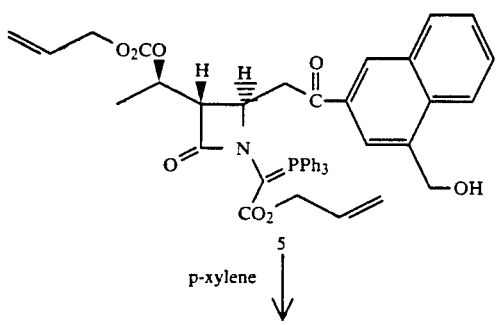

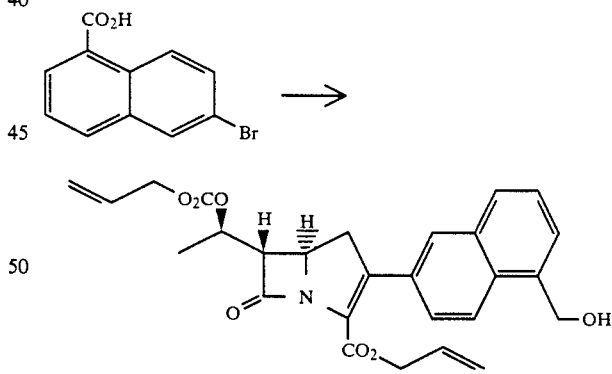

Allyl-(5R,6S)-2-(1-hydroxymethyl-3-naphthyl)-6-[1R-(allyloxycarbonyloxy)ethyl]-carbapen-2-em-3-carboxylate (6)

To solution of 2.5 g (3.3 mmoles) of azetidinone 5 in 300 ml anhydrous xylenes at room temperature under an argon atmosphere was added several crystals of hydroquinone. The solution was stirred 2 hours at 155° under an argon atmosphere and then cooled to room temperature. The solution was concentrated under vaccum to a yellow paste and the crude product purified by column chromatography (45 g silica gel; packed and eluted with 3:2; hexanes:EtOAc) to provide 1.28 g of the title compound.

¹NMR (300 MHz, CDCl₃): δ 1.49 (d, J=5.8 Hz, CH₃CH), 1.96 (t, CH₂OH), 3.3 (dd, J=10.0, 18.1 Hz, CHCH₂C), 3.42 (m, CHCH₂C and CHCHC=O ) 4.31 (dt, J=4.4, 7.8 Hz, CHCHCH₂), 4.67 (m, CH₃CHCH and CH₂CH=CH₂), 5.12 (d, J=5.4 Hz, CH₂OH), 5.29 (m, CH₂CH=CH₂), 5.90 (m, CH₂CH=CH₂), 7.54 (m, naphthyl-H2, H6, H7) 7.78 (s, naphthyl-H4), 7.84 (dd, J=1.7, 8.4 Hz, naphthyl-H5) 8.05 ppm (d, J=8.6 Hz, naphthyl-H8);

IR (CH₂Cl₂): 1780, 1745, 1720 cm⁻¹.

UV (dioxane): λ_max=288, 325 nm.

EXAMPLE 6

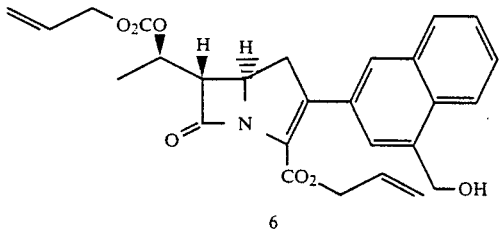

Allyl-(5R, 6S)-2-(1-hydroxymethyl-6-naphthyl)-6-[1R-(allyloxycarbonyloxy)ethyl]-carbapen-2-em-3-carboxylate (7)

In an analogous manner to that described in Examples 1-5, but starting with 6-bromo-1-naphthoic acid [M. J. S. Dewar and P. J. Grisdale, J. Amer. Chem. Soc. 84, 3541 (1962)], the title compound was obtained as a pale yellow foam.

¹H-NMR (300 MHz, CDCl₃): δ 1.47 (d, J=6.35 Hz, 3H, CH₃), 3.25 (dd, J=9.8, 18.1 Hz, 1H, H1a), 3.37 (dd, J=9.0, 18.1 Hz, 1H, H1b), 3.42 (dd, J=8.2, 2.8 Hz, 1H,

H5), 4.28 (dt, J=2.8, 9.4 Hz, 1H, H6), 4.55-4.75 (m, 4H, —OCH₂C=C), 5.08 (bs, 2H, ArCH₂O), 5.1-5.4 (m, 5H, H8, —C=CH₂), 5.75-6.0 (m, 2H, —CH=C), 7.4-7.55 (m, 3H, ArH), 7.79 (d, J=10.9 Hz, 1H, ArH), 7.83 (s, 1H, ArH), 8.04 ppm (d, J=8.79, 1H, ArH), IR (CHCl₃): 3610 (OH), 1780 (β-lactam), 1745 (carbonate), 1725 cm⁻¹ (ester).

FAB-MS: m/e=478 (M+H).

EXAMPLE 7

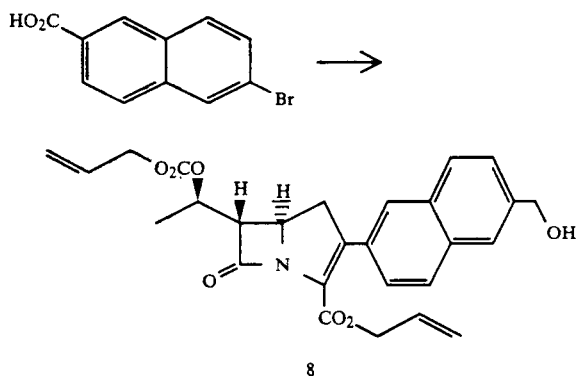

Allyl-(5R, 6S)-2-(2-hydroxymethyl-6-naphthyl)-6-[1R-(allyloxycarbonyloxy)ethyl]-carbapen-2-em-3-carboxylate (8)

In analogous manner to that described in Examples 1-5, but starting with 6-bromo-2-naphthoic acid [L. G. Anderson and D. Johnston, J. Amer. Chem. Soc. 65, 239 (1943)], the title compound was obtained as a white foam.

¹H-NMR (300 MHz, CDCl₃): δ 1.50 (d, J=6.77 Hz, 3H, CH₃), 3.25-3.55 (m, 2H, H1), 3.45 (dd, J=13.2, 2.7 Hz, 1H, H6), 4.32 (dt, J=2.7, 9.5 Hz, 1H, H5), 4.55-475 (m, 4H, —OCH₂C=C), 4.86 (d, J=5.37 Hz, 2H, ArCH₂O), 5.1-5.4 (m, 5H, H8, —C=CH₂), 5.75-6.0 (m, 2H, —CH=C), 7.4-7.5 (m, 2H, ArH), 7.7-7.85 ppm (m, 4H, ArH).

IR (CHCl₃): 3600 (OH), 1780 (β-lactam), 1745 (carbonate), 1725 cm⁻¹ (ester).

FAB-MS: m/e=478 (M+H).

EXAMPLE 8

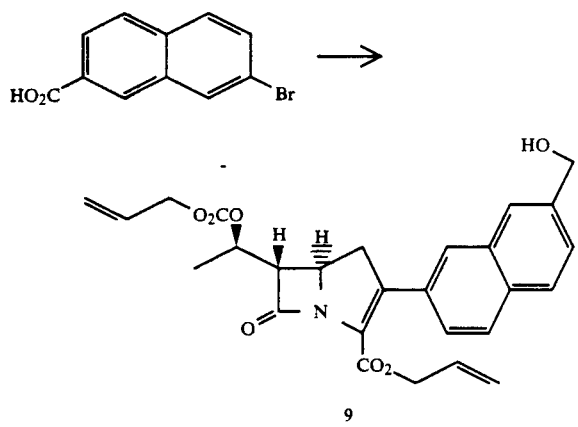

Allyl-(5R,6S)-2-(2-hydroxymethyl-7-naphthyl)-6-[1R-(allyloxycarbonyloxy)ethyl]-carbapen-2-em-3-carboxylate (9)

In a analogous manner to that described in Examples 1-5, but starting with 7-bromo-2-naphthoic acid [W. Adcock and P. R. Wells Aust. J. Chem. 18, 1351 (1965)], the title compound was obtained as a pale yellow foam.

¹H-NMR (300 MHz, CDCl₃): δ 1.49 (d, J=6.35 Hz, 3H, CH₃), 3.28 (dd, J=9.9, 18.1 Hz, 1H, H1a), 3.39 (dd, J=8.9, 18.1 Hz, 1H, H1), 3.44 (dd, J=8.4, 2.8 Hz, 1H, H6), 4.32 (dt, J=2.8, 9.3 Hz, 1H, H5), 4.55-4.75 (m, 4H, —OCH₂C=C), 4.85 (d, J=5.62 Hz, Hz, 2H, ArCH₂O), 5.1-5.4 (m, 5H, H8, —C=CH₂), 5.75-6.0 (m, 2H, —CH=C), 7.4-7.55 (m, 2H, ArH), 7.75-7.85 ppm (m, 4H, ArH).

IR(CHCl₃): 3600 (OH), 1780 (β-lactam), 1745 (carbonate), 1725 cm⁻¹ (ester).

EXAMPLE 9

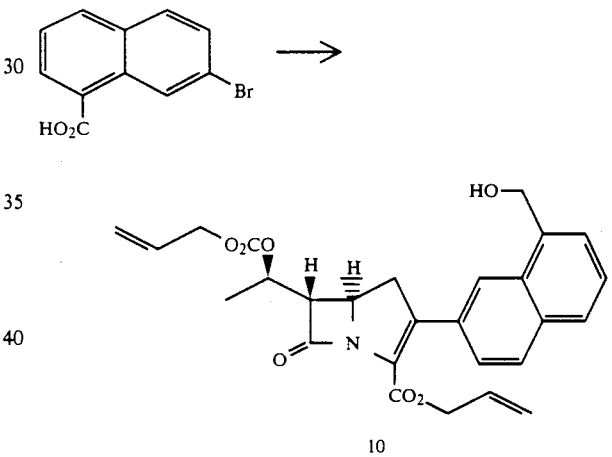

Allyl-(5R,6S)-2-(1-hydroxymethyl-7-naphthyl)-6-[1R-(allyloxycarbonyloxy)ethyl]-carbapen-2-em-3-carboxylate (10)

In analogous manner to that described in Examples 1-5, but starting with 7-bromo-1-naphthoic acid [H. Goldstein and H. A. Fischer, Helv. Chim. Acta 21, 1519 (1938)], the title compound was obtained as a white foam.

¹H-NMR (300 MHz, CDCl₃): δ 1.51 (d, J=6.35 Hz, 3H, CH₃), 3.3-3.5 (m, 2H, H1), 3.45 (dd, J=9.1, 2.8 Hz, 1H, H6), 4.33 (dt, J=2.8, 9.9 Hz, 1H, H5), 4.55-4.75 (m, 4H, —OCH₂C=C), 5.1 (d, J=6.25 Hz, 2H, ArCH₂O), 5.1-5.4 (m, 5H, H8, —C=CH₂), 5.75-6.0 (m, 2H, —CH=C), 7.4-7.55 (m, 3H, ArH), 7.75-7.85 (m, 2H, ArH), 8.20 ppm (s, 1H, ArH).

IR (CHCl₃): 3610 (OH), 1780 (β-lactam), 1745 (carbonate) 1725 cm⁻¹ (ester).

FAB-MS: m/e=478 (M+H).

EXAMPLE 10

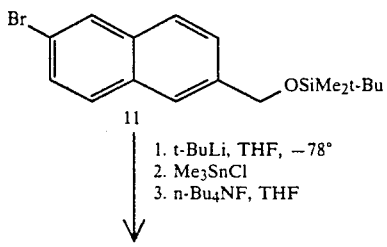

reaction with saturated NH₄Cl was followed by removal of the solvent in vacuo. The residual was dissolved in EtOAc and washed with water and brine, dried (MgSO₄), filtered and the solvent removed in vacuo. Purification by flash chromatography (30% EtOAc/hexanes) and crystallization from Et₂O/hexane at 0° C. provided 1.38 g (87%) of stannyl alcohol as a white solid. $^1$H-NMR (300 MHz, CDCl₃):δ 0.34 (s, 9H), 1.69 (t, J=5.5Hz, 1H), 4.85 (d, J=6.0 Hz, 2H), 7.46 (dd, J=8.5, 1.5 Hz, 1H), 7.57 (d, J=8.5 Hz, 1H), 7.75–7.81 (m, 3H), 7.94 ppm (s, 1H).

EXAMPLE 11

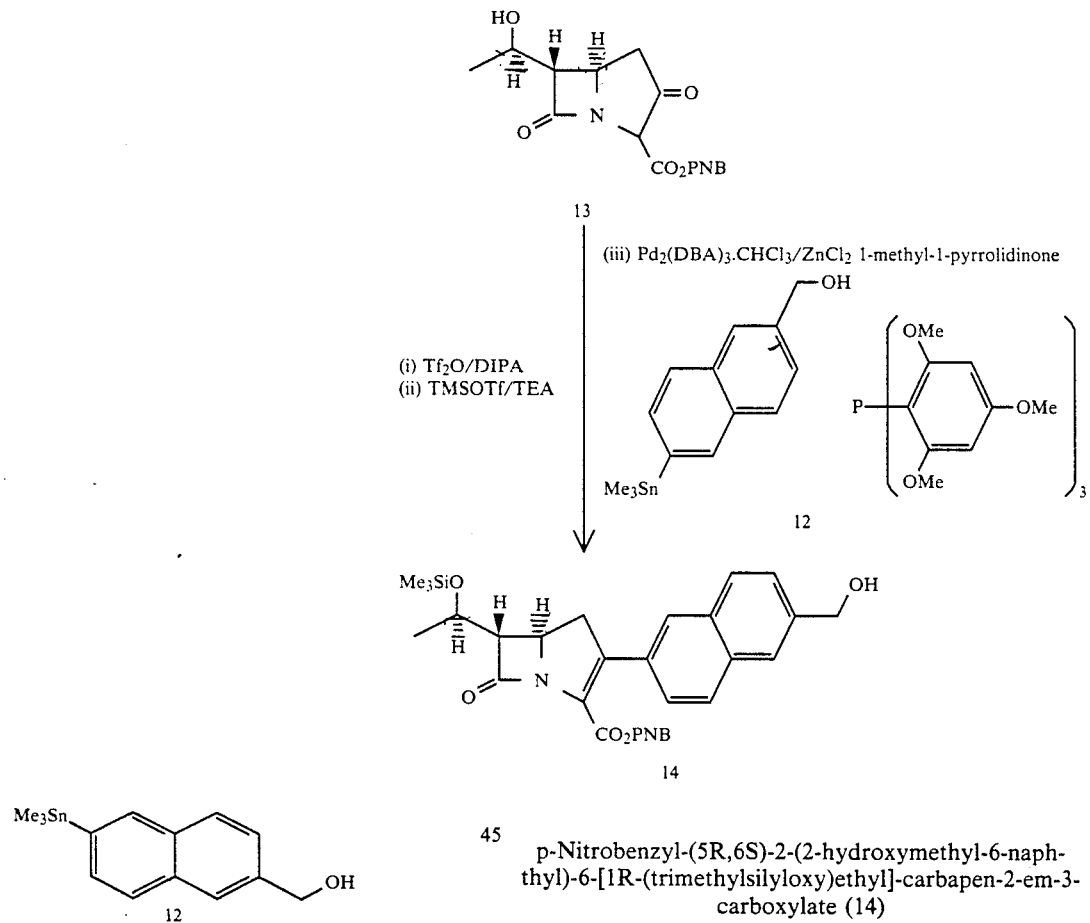

2-Trimethylstannyl-6-hydroxymethylnaphthalene (12)

Bromonaphthalene 11 (1.72 g, 4.9 mmol), prepared in analogous manner to that described in Examples 1 and 2, but starting with 6-bromo-2-naphthoic acid, was dissolved in anhydrous THF (30 mL) and cooled to −78° C. under nitrogen. To this stirred solution was added a 1.7M solution of t-BuLi in pentane (2.2 equiv.; 10.8 mmol; 6.3 mL). After 2.5 hours at −78° C., Me₃SnCl (1.2 equiv.; 5.88 mmol; 1.17 g) was added as a solid. The cold bath was removed and the reaction allowed to reach ambient temperature. After 4 hours, the reaction was quenched with water. The solvent was removed in vacuo and the residual dissolved in Et₂O. Washing with water and brine was followed by drying over MgSO₄, filtering and removal of solvent. The residual was dissolved in anhydrous THF and treated with a 1.0M solution of $^n$Bu₄NF in THF (1.1 equiv.; 5.4 mmol; 5.4 mL) at ambient temperature for 5 minutes. Quenching the p-Nitrobenzyl-(5R,6S)-2-(2-hydroxymethyl-6-naphthyl)-6-[1R-(trimethylsilyloxy)ethyl]-carbapen-2-em-3-carboxylate (14)

A dry 15 mL receiving flask was charged with the bicyclic β-ketoester 13 (143 mg; 0.41 mmol) and a magnetic stir bar and the system was purged with nitrogen. Two mL of anhydrous tetrahydrofuran (THF) was added and upon dissolution of 13, the reaction vessel was cooled to −78° C. under N₂. Diisopropylamine (0.063 mL, 0.45 mmol) was then added and the stirring was continued for 10 minutes. Trifluoromethane-sulfonic anhydride (0.075 mL, 0.45 mmol) was added, followed by stirring for additional 15 minutes. Triethylamine (0.062 mL. 0.45 mmol) was then added, followed by trimethylsilyl trifluoromethanesulfonate (0.087 mL, 0.45 mmol).

While the above reaction was stirred for 20 minutes, the organostannane 12 (144 mg, 0.45 mmol), tris(dibenzylideneacetone)dipalladium-chloroform (8.5 mg, 0.0082 mmol) and tris(2,4,6-trimethoxyphenyl)phosphine (17.4 mg, 0.033 mmol) were weighed into a single vial and the vial was purged with nitrogen. When the above reaction time had elapsed, N-methylpyrrolidinone (2 mL) was added to the initial reaction mixture followed by the previously weighed solids. A 0.87M zinc chloride in ether solution (0.52 mL, 0.45 mmol) was then added. The low temperature bath was then removed and the reaction vessel was placed in a luke warm water bath to allow it to quickly reach ambient temperature. After reaching ambient temperature, the mixture was stirred for 15 minutes. The reaction was then quenched by pouring the contents of the flask into a 125 mL separatory funnel containing diethyl ether, ethyl acetate and water. The organic phase was separated and washed with water and brine. The organic phase was dried over magnesium sulfate. The mixture was then filtered and the solvent removed under vacuum. Flash column chromatography of the residue (silica gel, 40% ethyl acetate/hexanes) provided 123 mg (54%) of the desired carbapenem.

$^1$H-NMR (300 MHz, CDCl$_3$): δ 0.14 (s, 9H), 1.30 (d, J=6.2 Hz, 3H), 1.89 (dd, J$_1$=J$_2$=6.1 Hz, 1H), 3.22–3.44 (complex m, 3H), 4.23–4.34 (complex m, 2H), 4.85 (d, J=6.1 Hz, 2H), 5.20 (ABq, J$_{AB}$=13.7 Hz, Δv$_{AB}$=54.5 Hz, 2H), 7.21 (d, J=8.7 Hz, 2H), 7.38 (dd, J=8.6, 1.7 Hz, 1H), 7.44 (dd, J=8.4, 1.6 Hz, 1H), 7.66–7.76 (complex m, 4H), 7.88 ppm (d, J=8.7 Hz, 2H).

IR (CHCl$_3$): 3600(w), 1770(s), 1720(m), 1600(m), 1520(s) cm$^{-1}$.

UV (CH$_3$CN): λ$_{max}$=320, ε=5000; λ$_{max}$=270, ε=7200.

EXAMPLE 12

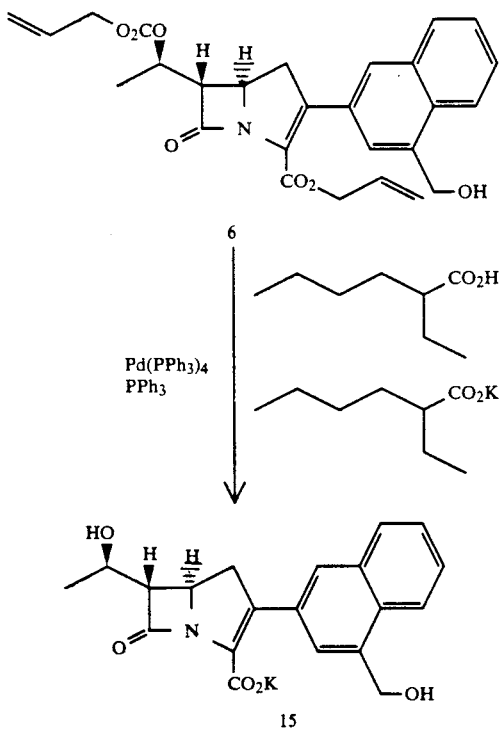

Potassium-(5R,6S)-2-(1-hydroxymethyl-3-naphthyl)-6-(1R-hydroxyethyl)carbapen-2-em-3-carboxylate (15)

To a stirred solution of 51.9 mg (0.11 mmoles) of the carbapenem 6 in 2 ml of anhydrous CH$_2$Cl$_2$ and 0.8 ml EtOAc was added a mixture of 25.2 mg (0.0218 mmoles) of tetrakis(triphenylphosphine)palladium and 17.2 mg (0.06 mmoles) of triphenylphosphine, followed by 19.2 μl (0.12 mmoles) of 2-ethylhexanoic acid and 240.4 μl (0.12 mmoles) of a 0.5 M potassium 2-ethylhexanoate in EtOAc solution. The resulting solution was stirred at room temperature for 3.5 hrs; a semi-transparent precipitate formed after 30 minutes. The reaction was then diluted with Et$_2$O and the solid was separated, washed twice with Et$_2$O and dried under vaccum to provide a greenish solid. The crude product was purified by reverse phase-PLC (1000μ 20×20 cm rev. phase silica gel F, eluted at 5° C. with 13% EtOH in H$_2$O). The UV active product band was extracted 8 times with CH$_3$CN:H$_2$O (4:1). The combined aqueous extracts were washed 3 times with hexanes, filtered through a Gelman Acrodisc-CR 0.45μ filter assembly and concentrated under vacuum. The concentrate was lyophilized to provide 34.2 mg of the title compound as a white fluffy solid.

$^1$H-NMR (200 MHz, D$_2$O): δ 1.34 (d, J=8.3 Hz, CH$_3$CHCH), 3.12 (dd, J=9.9, 16.8 Hz, CHCH$_2$C), 3.51 (m, CHCH$_2$C and CHCHC=O), 4.27 (m, CH$_3$CHCH and CHCHCH$_2$) 5.06 (s, naphthyl-CH$_2$), 7.53 (d, J=1.5 Hz, naphthyl-H2), 7.60 (m, naphthyl-H6 and H7), 7.78 (s, naphthyl-H4), 7.93 (m, naphthyl-H5), 8.08 ppm (m, naphthyl-H8);

IR (nujol): 1750, 1590 cm$^{-1}$.

UV(H$_2$O): λ$_{max}$=282, 317 nm.

EXAMPLE 13

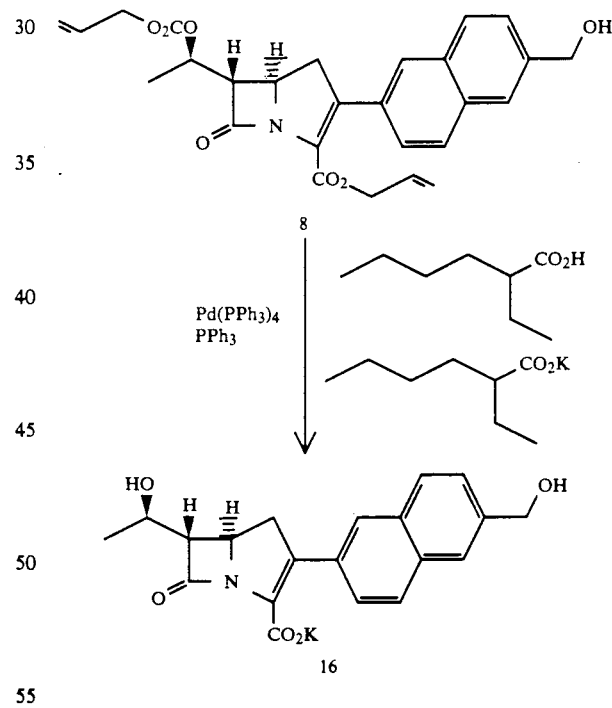

Potassium-(5R,6S)-2-(2-hydroxymethyl-6-naphthyl)-6-(1R-hydroxyethyl)-carbapen-2-em-3-carboxylate (16)

In an analogous manner to that described in Example 12, carbapenem 8 (119.2 mg, 0.250 mmol) was de-allylated to yield the title compound (47.2 mg, 48%) as an off-white lyophilized solid.

$^1$H-NMR (300 MHz, 2:1 D$_2$O/CD$_3$CN): δ 1.65 (d, J=6.35 Hz, 3H, CH$_3$), 3.50 (dd, J=9.7, 16.7 Hz, 3H, H1a), 4.75–4.95 (m, 2H, H1b, H6), 4.5–5.7 (m, 2H, H5, H8), 5.12 (s, 2H, —CH$_2$—O), 7.86 (d, J=8.5 Hz, 1H), 7.94 (d, J=8.7 Hz, 1H), 8.18 (s, 2H), 8.19 (d, 1H, partially obscured), 8.24 ppm (d, J=8.5 Hz, 1H).

IR (KBr): 1750 (β-lactam), 1590 cm⁻¹ (carboxylate).
UV(H₂O): $\lambda_{max}$=318 nm; $\epsilon$=17,500.

EXAMPLE 14

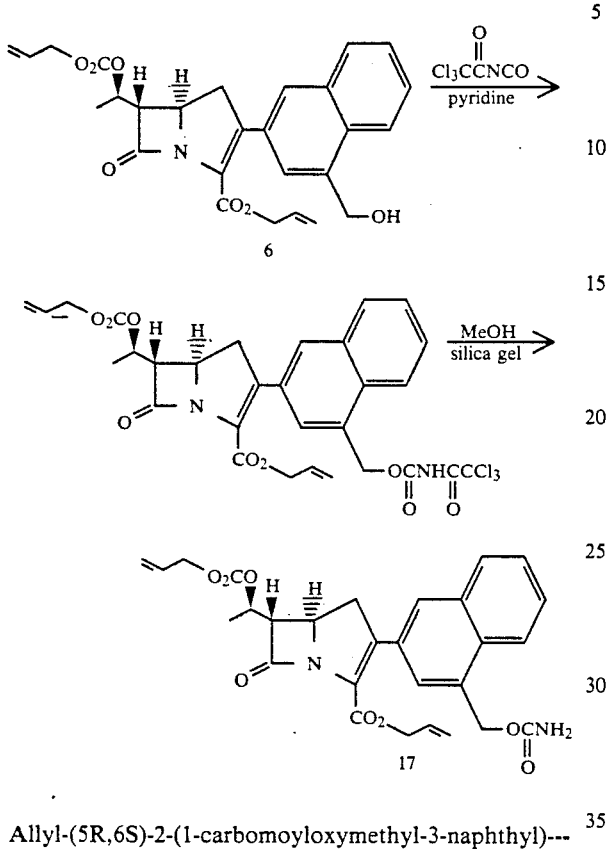

Allyl-(5R,6S)-2-(1-carbomoyloxymethyl-3-naphthyl)---6-[1R-(allyloxycarbonyloxy)ethyl]-1-carbapen--2-em-3-carboxylate. (17)

To a stirred solution of 49.7 mg (0.1 mmoles) of the previously described carbapenem 6 in 1.5 ml anhydrous CH₂Cl₂ at 0° under a N₂ atmosphere was added 25 μl (0.3 mmoles) of pyridine and 13.6 μl (0.133 mmoles) of trichloroacetyl isocyanate. The resulting solution was stirred at 0° under a N₂ atmosphere for 3 hours and then partitioned between EtOAc and ice/2.0N aqueous HCl solution. The organic phase was separated and washed with brine, dried with anhydrous Na₂SO₄, filitered and concentrated under vaccum to provide 80 mg of a yellow foam.

¹H-NMR (200 MHz, CDCl₃): δ 5.76 ppm (s, napht-hyl-CH₂).

IR (CH₂Cl₂): 3510, 3400, 1810, 1780, 1745 cm⁻¹.

The foam was dissolved in 1.5 ml anhydrous MeOH and to the resulting solution was added 611 mg of silica gel 60. The resulting mixture was stirred 1.75 hrs at room temperature and 18 hrs at 5° C. under N₂ atmosphere. The reaction mixture was then filtered and the silica gel rinsed with methanol. The combined filtrates were concentrated under vaccum to give a clear film which was purified by silica gel PLC (1000 μ 20×20 cm GF plates, eluted with 3:1; CH₂Cl₂:EtOAc) to provide 43.8 mg of the title compound as a clear film.

¹H-NMR (200 MHz, CDCl₃): δ 1.49 (d, J=6.4 Hz, CH₃CHCH), 3.27 (dd, J=9.8, 18.0 Hz, CHCHCH₂), 3.39 (dd, J=8.4, 18 Hz, CHCHCH₂), 3.43 (dd, J=2.9, 8.3 Hz, CHCHC=O), 4.34 (dt, J=2.9, 9.3 Hz, CHCHCH₂), 4.66 (m, CH₃CHCH and CH₂CH=CH₂), 4.80 (bs, NH₂), 5.27 (m, CH₂CH=CH₂), 5.53 (s, napht-hyl-CH₂), 5.90 (m, CH₂CH=CH₂), 7.51 (m, 3×naphthyl-H), 7.83 (s, naphthyl H4), 7.84 (d, naphthyl-H5), 7.99 ppm (d, J=7.3 Hz, naphthyl H8);

IR (CH₂Cl₂): 3530, 3430, 1780, 1740 cm⁻¹.

UV(dioxane): $\lambda_{max}$=287, 324 nm.

EXAMPLE 15

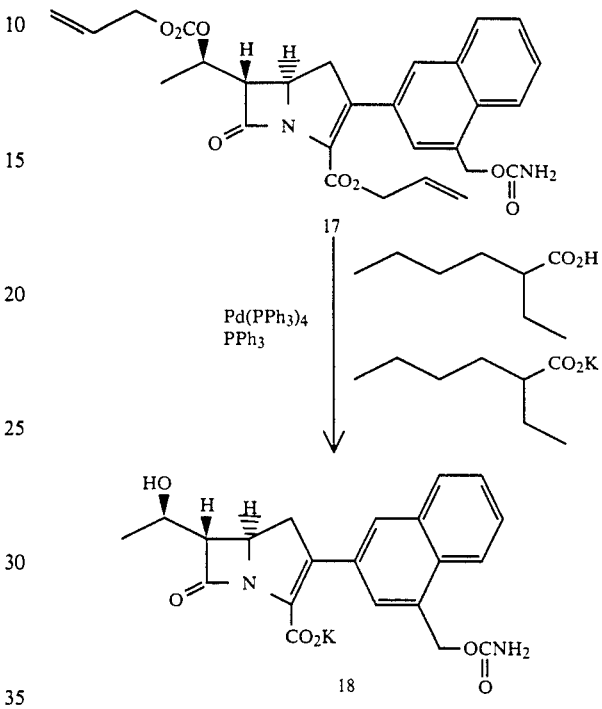

Potassium-(5R,6S)-2-(1-carbamoyloxymethyl-3-naphthyl)-6-[1R-hydroxyethyl]-1-carbapen-2-em-3-carboxylate (18)

To a stirred solution of 43.7 mg (0.083 mmoles) of 17 in 1.6 ml anhydrous CH₂Cl₂ and 0.5 ml EtOAc was added a mixture of 17.1 mg (0.016 mmoles) of tetrakis(-triphenylphosphine)palladium and 13.0 mg (0.05 mmoles) of triphenylphosphine, followed by 14.5 μl (0.09 mmoles) of 2-ethylhexanoic acid and 182.1 μl (0.09 mmoles) of a 0.5M potassium 2-ethylhexanoate in EtOAc solution. The resulting mixture was stirred at room temperture under a N₂ atmosphere for 2.75 hrs and at 0° for 2 hrs. The reaction mixture was then diluted with EtOAc and the solid separated and washed 2 times with Et₂O. The solid was then dried under vacuum and purified by reverse phase-PLC (1000μ, 20×20 cm rev. phase silica gel F, eluted at 5° C. with 13% EtOH in H₂O). The UV active product band was extracted 8 times with CH₃CN:H₂O (4:1). The combined aqueous extracts were washed 3 times with hexanes, filtered through a Gelman Acrodisc-CR 0.45μ filter assembly and concentrated under vacuum. The concentrate was lyophilized to give 25.4 mg of the title compound as a fluffy white solid.

¹H-NMR (300 MHz, D₂O): δ 1.33 (d, J=5.8 Hz, CH₃CHCH), 3.07 (dd, J=9.3, 17.0 Hz, CH₂CHCH), 3.41 (dd, J=8.0, 16.1 Hz, CH₂CHCH), 3.50 (m, CHCHC=O), 4.27 (m, CH₃CHOH and CHCHCH₂), 5.46 (s, naphthyl-CH₂), 7.53 (s, naphthyl-H₂), 7.58 (m, naphthyl-H6 and H7), 7.77 (s, naphthyl-H4), 7.91 (d, J=7.0 Hz, naphthyl-H5), 7.98 ppm (d, J=9.0 Hz, naphthyl-H8);

IR (nujol): 1720, 1600 cm$^{-1}$.

UV(H$_2$O): $\lambda_{max}$=283, 318 nm.

EXAMPLE 16

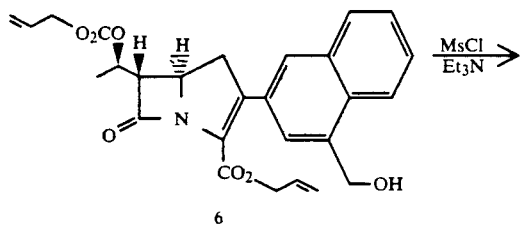

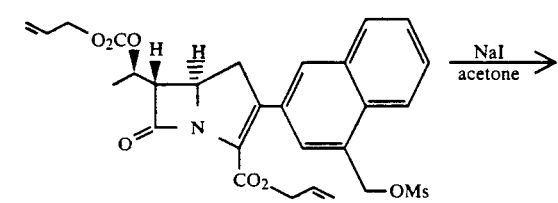

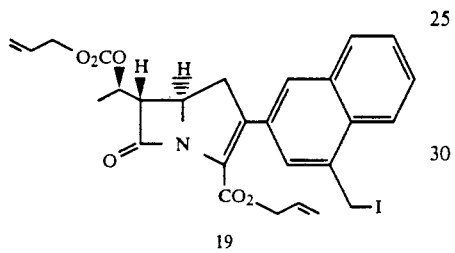

Allyl-(5R,6S)-2-(1-iodomethyl-3-naphthyl)-6-[1R-(allyloxycarbonyloxy)ethyl]-carbapen-2-em-3-carboxylate (19)

To a solution of 107.0 mg (0.225 mmoles) of carbapenem 6 in 4 ml anhydrous CH$_2$Cl$_2$ at −20° C. under a N$_2$ atmosphere was added triethylamine (50.1 μl, 0.36 mmoles), followed by mesyl chloride (22.7 μl, 0.29 mmoles). The resulting solution was stirred at −20° under N$_2$ atmosphere for 30 minutes and then partitioned between CH$_2$Cl$_2$ and ice/2.0N aqueous HCl solution. The organic phase was separated and washed with brine, dried with anhydrous Na$_2$SO$_4$, filtered and concentrated under vacuum to provide 154.5 mg of a clear film.

$^1$H-NMR (300 MHz, CDCl$_3$): δ 2.88 (s, CH$_3$SO$_2$), 5.68 (s, CH$_2$OSO$_2$).

The crude reaction residue was dissolved in 4 ml anhydrous acetone and sodium iodide (67.5 mg, 0.45 mmoles) was added to the resulting solution. The solution was stirred at room temperature for 1.5 hrs and then partitioned between CH$_2$Cl$_2$ and ice/0.5M aqueous Na$_2$S$_2$O$_3$ solution. The organic phase was separated and washed with brine, dried with anhydrous Na$_2$SO$_4$, filtered and concentrated under vacuum to provide a yellow film. The crude reaction residue was purified by thin layer chromatography (2×1000μ 20×20 cm silica gel, eluted with 4% EtOAc in CH$_2$Cl$_2$) to provide 128.4 mg of the title compound as a yellow foam.

$^1$H-NMR (300 MHz CDCl$_3$): δ 1.51 (d, J=6.8 Hz, CH$_3$CHCH), 3.31 (dd, J=9.9, 18.2 Hz, CH$_2$CHCH), 3.41 (dd, J=8.7, 18.1 Hz, CH$_2$CHCH), 3.46 (dd, J=2.7, 8.2 Hz, CH$_2$CHCH), 4.33 (dt, J=2.8, 9.2 Hz CHCHCH$_2$), 4.70 (m, CH$_2$CH=CH$_2$ and CH$_3$CHCH), 4.87 (s, naphthyl-CH$_2$I), 5.3 (m, CH$_2$CH=CH$_2$), 5.91 (m, CH$_2$CH=CH$_2$), 7.43 (t, J=7.1, 7.7 Hz, naphthyl-H6), 7.59 (d, J=1.7 Hz, naphthyl-H1), 7.67 (t, J=7.0, 7.1 Hz, naphthyl-H7), 7.80 (s, naphthyl-H4); 7.76 (d, J=8.2 Hz, naphthyl-H5), 8.07 ppm (d, J=8.1 Hz, naphthyl-H8).

IR (CH$_2$Cl$_2$): 1780, 1745, 1720 cm$^{-1}$.

EXAMPLE 17

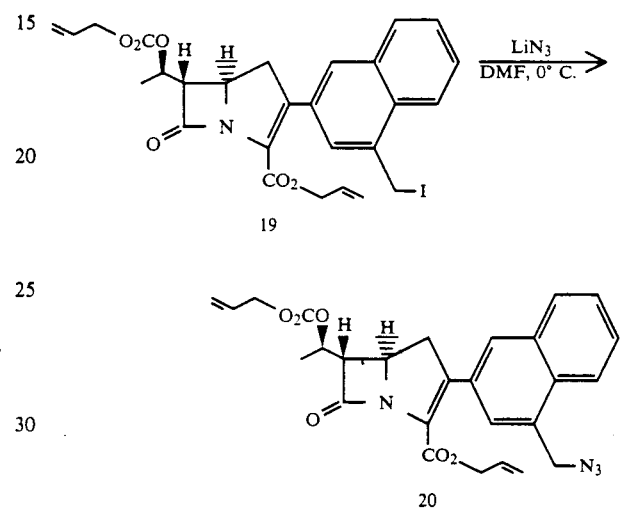

Allyl-(5R,6S)-2-(1-azidomethyl-3-naphthyl)-6-[1R-(alloyloxycarbonyloxy)ethyl]-carbapen-2-em-3-carboxylate. (20)

To a stirred solution of 78.9 mg (0.135 mmoles) of the iodide 19 in 3 ml anhydrous DMF at 0° under a N$_2$ atmosphere was added 13.2 mg (0.27 mmoles) of lithium azide. The resulting solution was stirred at 0° under a N$_2$ atmosphere for 30 minutes and then was partitioned between EtOAc and ice/H$_2$O. The organic phase was separated and washed four times with ice/H$_2$O and then with brine. The organic phase was dried with anhydrous Na$_2$SO$_4$, filtered and concentrated under vacuum to provide 67.8 mg of the title compound as a yellow foam.

$^1$H-NMR (200 MHz, CDCl$_3$): δ 1.52 (d, J=6.4 Hz, CH$_3$CHCH) 3.30 (dd, J=10.2, 17.5 Hz, CH$_2$CHCH), 3.44 (m, CH$_2$CHCH), 3.467 (dd, J=2.5, 8.2 Hz, CHCHC=O), 4.35 (dt, J=3.3, 9.1 Hz, CHCHCH$_2$), 4.67 (m, CH$_3$CHCH and CH$_2$CH=CH$_2$), 4.77 (s, naphthyl-CH$_2$), 7.49 (s, naphthyl-H2), 7.58 (m, naphthyl-H6 and H7), 7.84 (s, naphthyl-H4), 7.86 (d, naphthyl-H5), 7.99 ppm (d, J=8.0 Hz; naphthyl-H8).

IR (CH$_2$Cl$_2$): 2110, 1780, 1748, 1725 cm$^{-1}$.

UV(dioxane): $\lambda_{max}$=289, 326 nm.

EXAMPLE 18

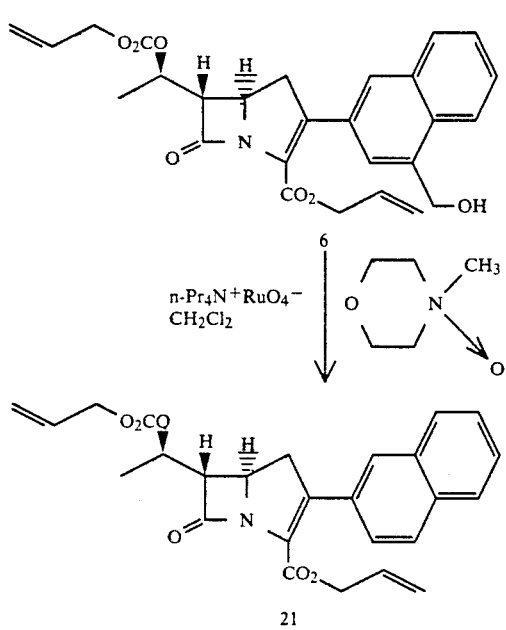

Allyl-(5R,6S)-2-(1-formyl-3-naphthyl-6-[1R-(allyloxycarbonyloxy)ethyl]-carbapen-2-em-3-carboxylate (21)

To a solution of the alcohol 6 (100 mg, 0.212 mmol) in 2.5 ml of methylene chloride were added N-methylmorpholine-N-oxide (37.3 mg, 0.318 mmol) and powdered 4 Å molecular sieves (10 mg). The mixture was stirred at room temperature for 10 minutes and then 3.7 mg (0.01 mmol) of tetra-n-propylammonium peruthenate (TPAP) was added. The reaction was monitored by TLC, and two additional portions of TPAP (3.7 and 5 mg) were added in order to complete the reaction. After 30 minutes, the reaction mixture was filtered through 3 g of silica gel. eluting with ethyl acetate. Evaporation of the filtrate yielded 85 mg (85%) of the title compound as a yellow oil.

$^1$H-NMR(300 MHz, CDCl$_3$): δ 1.49 (d, J=6.3Hz, 3H, CH$_3$), 3.25-3.50 (m, 3H, H1, H6), 4.35 (ddd, J=2.8, 9.0, 9.7 Hz, 1H, H5), 4.55-4.80 (m, 4H, —OCH$_2$C=C), 5.1-5.4 (m, 5H, H8, —C=CH$_2$), 5.75-6.00 (m, 2H, —CH=C), 7.60 (dd, J=7.6, 1.2 Hz, 1H), 7.69 (dd, J=8, 1.5 Hz, 1H), 7.87 (d, J=7.6Hz, 1H), 8.0 (d, J=1.8 Hz, 1H), 8.05 (bs, 1H), 9.18 (d, J=8.2 Hz, 1H), 10.3 ppm (s, 1H, CHO).

EXAMPLE 19

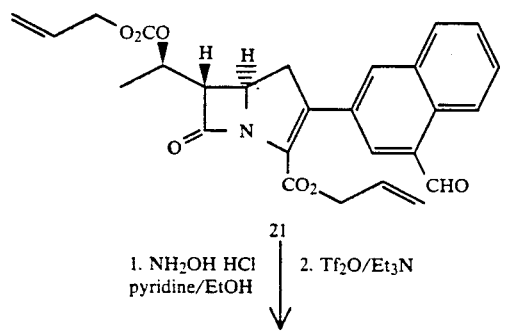

Allyl-(5R,6S)-2-(1-cyano-3-naphthyl)-6-[1R-(allyloxycarbonyloxy)ethyl]-carbapen-2-em-3-carboxylate (22)

To a solution of the aldehyde 21 (83 mg, 0.174 mmol) in ethanol (0.88 ml) and pyridine (0.88 ml) at 0° C. was added hydroxylamine hydrochloride (11.8 mg. 0.174 mmol). After 10 minutes the reaction mixture was diluted with ethyl acetate and washed successively with saturated NH$_4$Cl, H$_2$O, and brine. Drying over MgSO$_4$ and evaporation gave a yellow foam which was dissolved in methylene chloride and cooled to −70° C. Triethylamine (0.051 ml, 0.37 mmol) was added followed by triflic anhydride (0.029 ml, 0.17 mmol). After 10 minutes, the red reaction mixture was diluted into ethyl acetate and the solution was washed successively with saturated NH$_4$Cl, saturated NaHCO$_3$, H$_2$O, and brine. Drying over MgSO$_4$ and evaporation gave an oil which was purified by flash chromatography through 8 g of silica gel (7:3 ethyl acetate/hexane) to yield 71.6 mg (90%) of the title compound as a yellow foam.

$^1$H-NMR (300 MHz, CDCl$_3$): δ 1.49 (d, J=6.4 Hz, 3H, CH$_3$), 3.25-3.45 (m, 2H, H1), 3.47 (dd, J=2.9, 8.3 Hz, 1H, H6), 4.35 (ddd, J=2.9, 9.0, 9.7 Hz, 1H, H5), 4.45-4.80 (m, 4H, —OCH$_2$C=C), 5.1-5.4 (m, 5H, H8, —C=CH$_2$), 5.75-6.0 (m, 2H,—CH=C), 7.55-7.75 (m, 2H), 7.8-8.0 (m,2H) 8.0 (s, 1H), 8.2 ppm (d, J=8.2 Hz, 1H).

IR (CHCl$_3$): 2230 (nitrile), 1780 (β-lactam), 1740 (carbonate), 1730 cm$^{-1}$ (ester).

EXAMPLE 20

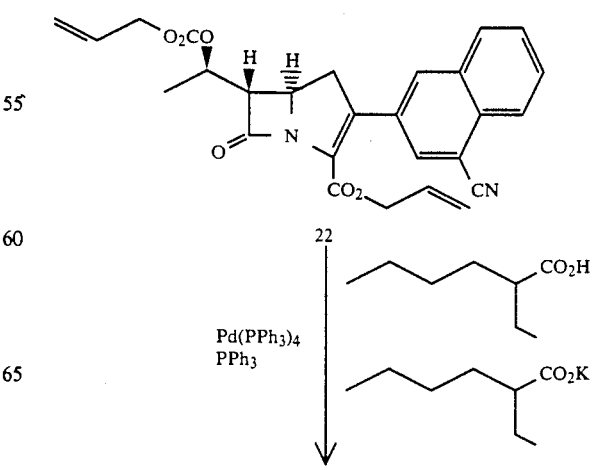

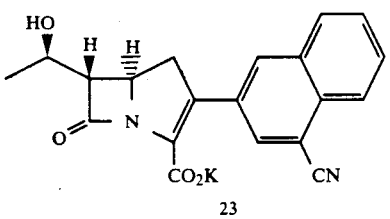

Potassium (5R,6S)-2-(1-cyano-3-naphthyl)-6-(1R-hydroxyethyl)-carbapen-2-em-3-carboxylate (23)

To a solution of the carbapenem 22 (71.6 mg, 0.156 mmol) in 1:1 ethyl acetate-methylene chloride (2.4 ml) at 0° C. were added in sequence a solution of potassium 2-ethylhexanoate in ethyl acetate (0.5M, 0.312 ml), a solution of the 2-ethylexanoic acid in methylene chloride (1.0M, 0.156 ml), triphenylphosphine (12 mg, 0.046 mmol), and tetrakis(triphenylphosphine)palladium (18 mg, 0.016 mmol). The mixture was sonicated for 30 seconds in an ultrasonic bath and was then stirred at 0° C. for 1 hour. The reaction was pipetted into a centrifuge tube containing cold ethyl ether and the solid was isolated by centrifugation, washing twice with ethyl ether. After drying under a stream of nitrogen and then in vacuo, 66 mg of an orange solid was obtained. Purification by reverse-phase preparative TLC (4:1 $H_2O/CH_3CN$) yielded 10.1 mg (18%) of a pale orange lyophilized solid.

$^1$H-NMR (300 MHz, 2:1 $D_2O/CD_3CN$): δ 1.62 (d, J=6.3 Hz, 3H, CH$_3$), 3.49 (dd, J=9.7, 17 Hz, 1H, H1a), 3.75-3.90 (m, 2H, H1b, H6), 4.45-4.70 (m, 2H, H5, H8), 7.95-8.15 (m, 2H), 8.34 (d, J=7.8 Hz, 1H), 8.43(s, 1H), 8.45 (d, 1H, obscured), 8.47 ppm (s, 1H).

IR(KBr): 2230 (nitrile), 1750 (β-lactam), 1595 cm$^{-1}$ (carboxylate).

UV($H_2O$): $\lambda_{max}$=293 nm, ε=14,000.

EXAMPLE 21

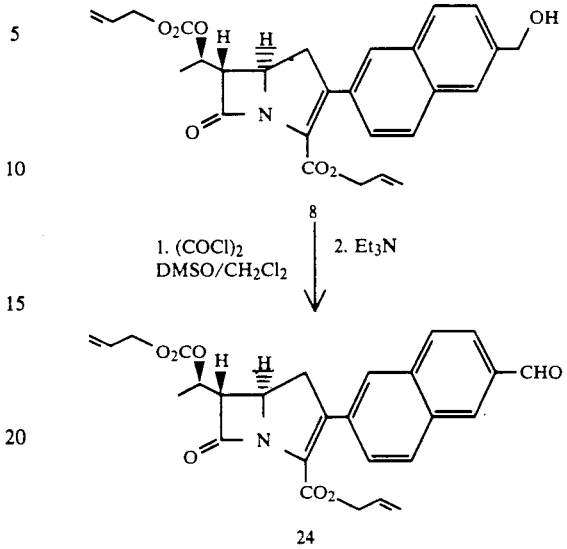

Allyl-(5R,6S)-2-(2-formyl-6-naphthyl)-6-[1R-(allyloxycarbonyloxy)ethyl]-carbapen-2-em-3-carboxylate (24)

To a stirring solution of oxalyl chloride (0.023 ml, 0.24 mmol) in 1.5 ml of methylene chloride at −70° C. was added neat dimethylsulfoxide (0.023 ml, 0.32 mmol). After 5 minutes, a solution of the alcohol 8 (113 mg, 0.237 mmol) in 0.5 ml of methylene chloride was added dropwise. The reaction mixture was stirred at −70° C. for 15 minutes and then triethylamine (0.091 ml, 0.65 mmol) was added. The temperature was maintained at −70° C. for 5 minutes more, and was then allowed to warm gradually to 0° C. during 2 hours. The reaction mixture was quenched with pH 7 phosphate buffer and was then diluted with ethyl acetate and washed successively with pH 7 phosphate buffer, water (2×) and brine. Drying (MgSO$_4$) and evaporation gave 105 mg (93%) of the title aldehyde as an oil which required no purification.

$^1$H-NMR (300 MHz, CDCl$_3$): δ 1.51 (d, J=5.61 Hz, 3H, CH$_3$), 3.25-3.50 (m, 3H, H6, H1), 4.36 (dt, J=2.75, 9.4 Hz, 1H, H5), 4.55-4.8 (m, 4H, —OCH$_2$C═C), 5.1-5.4 (m, 5H, H8, —C═CH$_2$), 5.75-6.0 (m, 2H, —CH═C), 7.56 (d, J=8.61 Hz, 1H, ArH), 7.8-8.0 (m, 4H, ArH), 8.32 (s, 1H, ArH), 10.16 ppm (s, 1H, CHO).

EXAMPLE 22

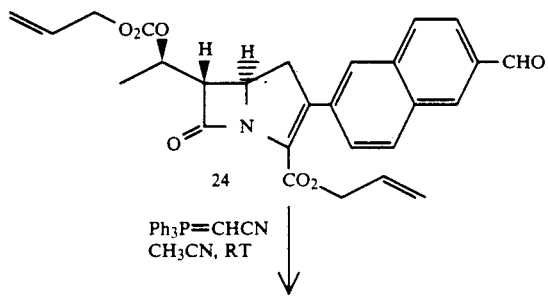

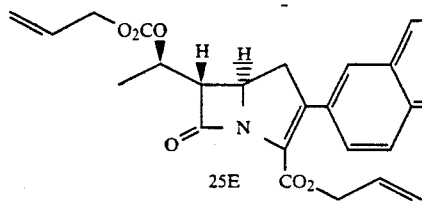
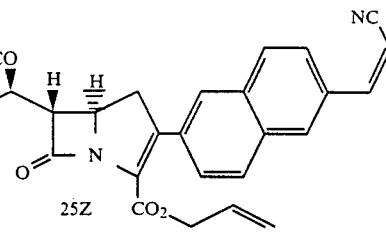

Allyl-(5R,6S)-2-{2-[E-2-(cyano)vinyl]-6-naphthyl}-6-[1R-(allyloxycarbonyloxy)ethyl]-carbapen-2-em-3-carboxylate (25E) and Allyl-(5R,6S)-2-{2-[Z-2-(cyano)vinyl]-6-naphthyl}-6-[1R-(allyloxycarbonyloxy)ethyl]-carbapen-2-em-3-carboxylate (25Z)

To a solution of aldehyde 24 (68 mg, 0.14 mmol) in 2 ml of acetonitrile was added (cyanomethylene)triphenylphosphorane (69 mg, 0.23 mmol). The reaction mixture was stirred at room temperature for 3 hours and was then evaporated in vacuo. Separation of the product mixture by HPLC (50 cm Whatman Partisil 10 silica M9 column, elution with 1:4 EtOAc/hexane at 6 ml/min) gave the faster eluting E-isomer 25E (29 mg, 40%) and the more polar Z-isomer 25Z (12 mg, 17%) as colorless oils.

25E:

$^1$H-NMR (300 MHz, CDCl$_3$): δ 1.51 (d, J=6.41 Hz, 3H, CH$_3$), 3.25-3.45 (m, 2H, H1), 3.47 (dd, J=8.3, 2.8 Hz, 1H, H6), 4.34 (dt, J=2.8, 9.4 Hz, 1H, H5), 4.6-4.8 (m, 4H, —OCH$_2$C≡C) 5.1-5.4 (m, 5H, H8, —C=CH$_2$), 5.8-6.0 (m, 2H, —CH=C), 5.99 (d, J=16.7 Hz, 1H, C=CHCN), 7.54 (d, J=16.7 Hz, 1H, CH=CCN), 7.45-7.60 (m, 2H, ArH), 7.75-7.85 ppm (m, 4H, ArH).

IR (CHCl$_3$): 1780 (β-lactam), 1745 (carbonate), 1725 (ester), 1620 cm$^{-1}$ (olefin).

FAB-MS: m/e=499 (M+H).

25Z:

$^1$H-NMR (300 MHz, CDCl$_3$): δ 1.51 (d, J=6.41 Hz, 3H, CH$_3$), 3.25-3.45 (m, 2H, H1), 3.47 (dd, J=2.9, 8.4 Hz, 1H, H6), 4.35 (dt, J=2.9, 9.4 Hz, 1H, H5), 4.6-4.8 (m, 4H, —OCH$_2$C≡C), 5.1-5.4(m, 5H, H8, —C=CH$_2$), 5.54 (d, J=12.1 Hz, 1H, C=CHCN), 5.75-6.0 (m, 2H, —CH=C), 7.27 (d, J=12.1 Hz, 1H, —CH=CCN), 7.51 (dd, J=8.5, 1.7 Hz, 1H, ArH), 7.8-7.9 (m, 3H, ArH), 8.04 (dd, J=8.6, 1.7 Hz, 1H, ArH), 8.15 ppm (s, 1H, ArH).

IR (CHCl$_3$): 1780 (β-lactam), 1745 (carbonate), 1725 (ester), 1610 cm$^{-1}$ (olefin).

FAB-MS: m/e=499 (M+H).

EXAMPLE 23

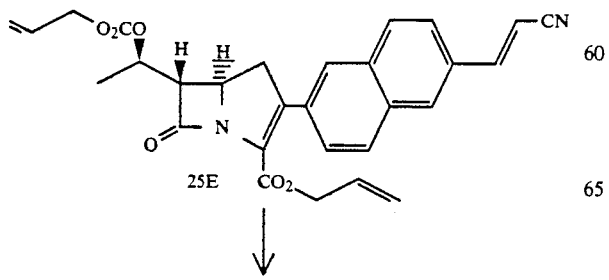

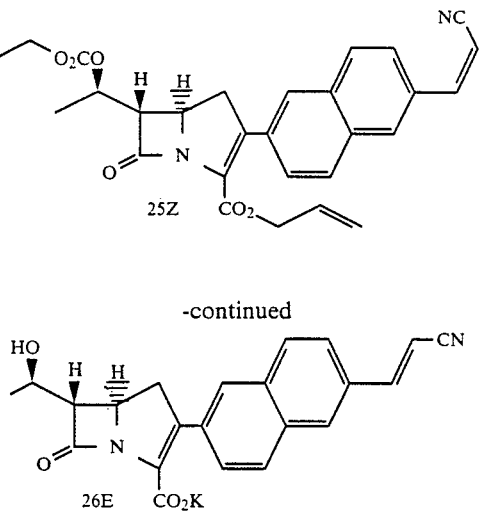

Potassium (5R,6S)-2-{2-[E-2-(cyano)vinyl]-6-naphthyl}-6-(1R-hydroxyethyl)-carbapen-2-em-3-carboxylate (26E)

In a manner analogous to that described in Example 20, carbapenem 25E (29 mg, 0.058 mmol) was de-allylated to yield the title carbapenem (13 mg, 54%) as a white lyophilized solid.

$^1$H-NMR (300 MHz, D$_2$O): δ 1.35 (d, J=5.93 Hz, 3H, CH$_3$), 2.8-3.0 (m, 1H, H1a), 3.25-3.40 (m, 1H, H1b), 3.48 (bs, 1H, H6), 4.2-4.4 (m, 2H, H8, H5), 5.85 (d, J=6.48 Hz, 1H, C=CHCN), 7.15-7.60 ppm (m, 7H, ArH, CH=CCN).

IR (KBr): 2220 (CN), 1750 (β-lactam), 1600 cm$^{-1}$ (carboxylate).

UV (H$_2$O): λ$_{max}$=343 nm, ε=26,200, 271, ε=29,200, 243, ε=26,500.

EXAMPLE 24

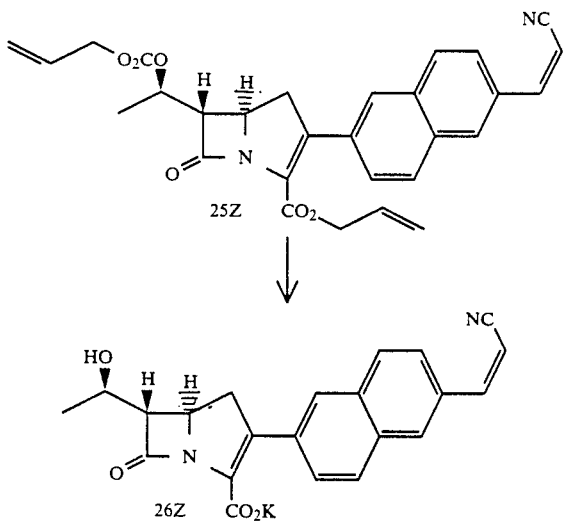

Potassium (5R,6S)-2-{2-[Z-2-(cyano)vinyl]-6-naphthyl}-6-(1R-hydroxyethyl)-carbapen-2-em-3-carboxylate (26Z)

In a manner analogous to that described in Example 20 carbapenem 25Z (12 mg, 0.024 mmol) was de-allylated to yield the title carbapenem (6.3 mg, 63%) as a white lyophilized solid.

¹H-NMR (300 MHz, D₂O): δ 1.37 (d, J=6.47 Hz), 3H, CH₃), 3.18 (dd, J=16.4, 10.0 Hz, 1H, H1a), 3.50–3.65 (m, 2H, H1b, H6), 4.25–4.45 (m, 2H, H8, H5), 5.73 (d, J=12.2 Hz, 1H, C=CHCN), 7.45–8.15 ppm (m, 7H, ArH, CH=CCN).

IR (KBr): 2220 (CN), 1650 (β-lactam), 1600 cm⁻¹ (carboxylate).

UV (H₂O): λ$_{max}$=343 nm, ε=24,800; 269 nm, ε=28,600; 242 nm, ε=26,000.

EXAMPLE 25

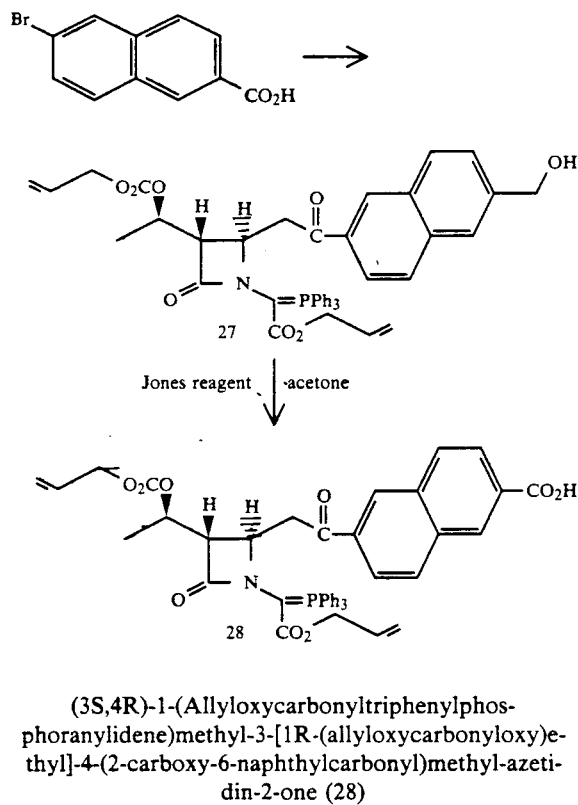

(3S,4R)-1-(Allyloxycarbonyltriphenylphos-phoranylidene)methyl-3-[1R-(allyloxycarbonyloxy)ethyl]-4-(2-carboxy-6-naphthylcarbonyl)methyl-azetidin-2-one (28)

(3S,4R)-1-(allyloxylcarbonyltriphenylphos-phoranylidene)methyl-3-[1R-(allyloxycarbonyloxy)-ethyl]-4-(2-hydroxymethyl-6-naphthylcarbonyl)methylazetidin-2-one 27 was prepared as described in Examples 1–4, but starting with 6-bromo-2-naphthoic acid [L. G. Anderson and D. Johnston, J. Amer. Chem. Soc. 65, 239 (1943)]. A solution of carbinol 27 (500 mg, 0.66 mmol) in acetone (12 ml) was cooled to 0° C. and Jones reagent (2N, 0.995 ml, 1.98 mmol) was added. After 30 minutes, the ice bath was removed, and the reaction was stirred for 6 hours at room temperature and then quenched with isopropyl alcohol and sodium sulfate. The mixture was filtered, evaporated to dryness in the presence of toluene, diluted into ethyl acetate and washed with water and brine. Drying (MgSO₄) and evaporation gave 467 mg of a solid which was purified by flash chromatography through 34 g of silica gel (10% methanol-methylene chloride) to yield 171 mg (33.5%) of the title compound.

¹H-NMR (300 MHz, CDCl₃): δ 1.17 ppm (d, J=6.04, 3H, —CH₃).

EXAMPLE 26

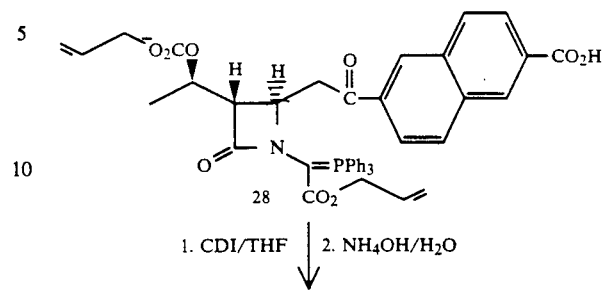

(3S,4R)-1-(allyloxycarbonyltriphenylphos-phoranylidene)methyl-3-[1R-(allyloxycarbonyloxy)ethyl]-4-(2-carbamoyl-6-naphthylcarbonyl)methyl-azetidin-2-one (29)

A solution of carboxylic acid 28 prepared in the preceding example (116 mg, 0.151 mmol) and 1,1'-carbonyldiimidazole (36 mg, 0.23 mmol) in 6 ml of tetrahydrofuran was stirred at room temperature. After 2 hours aqueous ammonium hydroxide (0.50M in 1:1 H₂O/THF, 3.0 ml) was added portionwise during 4 hours. The reaction mixture was diluted with ethyl acetate, and washed with water and brine. Drying (MgSO₄) and evaporation gave 88 mg of an oil which was purified by flash chromatography through 10 g of silica gel (10% methanol-methylene chloride to yield 46 mg (39%) of the title compound.

FAB-MS: m/e=769 (M+H).

¹H-NMR (300 MHz, CDCl₃): δ 1.17 ppm (d, J=6.29, 3H, —CH₃).

EXAMPLE 27

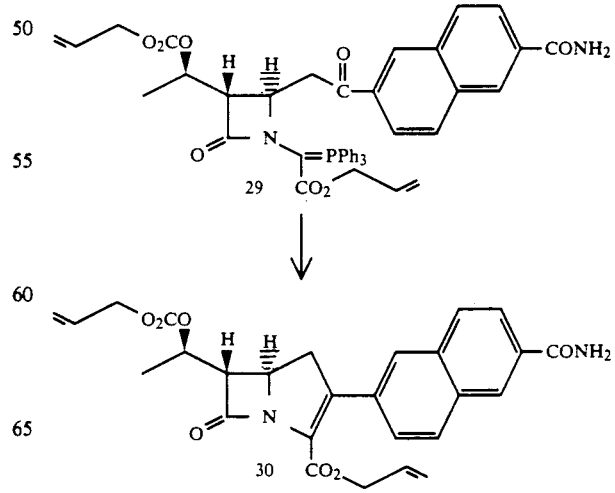

Allyl-(5R,6S)-2-(2-carbamoyl-6-naphthyl)-6-[1R-(allyloxycarbonyloxy)ethyl]-carbapen-2-em-3-carboxylate (30)

A solution of the carbamate 29 (40 mg, 0.052 mmol) in 3 ml of p-xylene was refluxed for 1.5 hours and then evaporated to dryness giving 29 mg of a yellow oil. Purification by preparative TLC on silica gel (7.5:2:0.5 ethyl acetate:methylene chloride:methanol) yielded 10 mg (31%) of the title carbapenem.

$^1$H-NMR (300 MHz, CDCl$_3$): δ 1.50 (d, J=6.35 Hz, 3H, —CH$_3$), 3.25–3.44 (m, 2H, H1a,b), 3.47 (dd, J=8.18, 2.86 Hz, 1H, H6), 4.34 (m, 1H, H5), 4.65–4.72 (m, 4H, C=C—CH$_2$—O), 5.13–5.40 (m, 5H, H8, CH$_2$=C), 5.75–6.05 (m, 2H, C=CH—), 6.1–6.4 (bs, 2H, —NH$_2$), 7.51 (dd, J=8.48, 1.64 Hz, 1H), 7.83–7.88 (m, 4H), 8.30 ppm (s, 1H).

IR (CH$_2$Cl$_2$): 1780 (β-lactam), 1750 (carbonate), 1720 (ester), 1680 cm$^{-1}$ (amide).

EXAMPLE 28

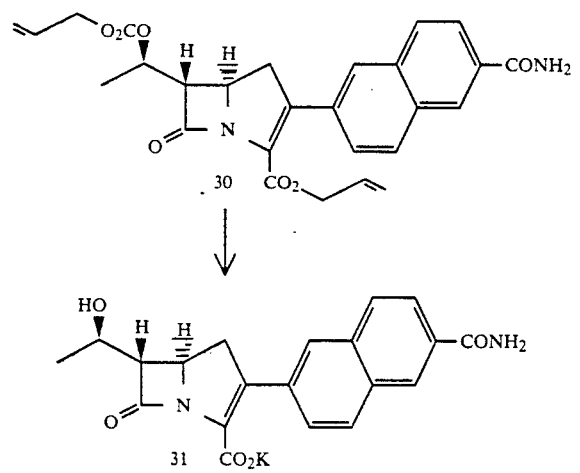

Potassium (5R,6S)-2-(2-carbamoyl-6-naphthyl)-6-(1R-hydroxyethyl)-carbapen-2-em-3-carboxylate (31)

To a solution of the carbapenem 30 (10 mg, 0.021 mmol) in ethyl acetate (0.17 ml) -methylene chloride (0.06 ml) were added in sequence potassium 2-ethylhexanoate (0.5M in EtOAc 0.042 ml, 0.021 mmol), 2-ethylhexanoic acid (1.0M in CH$_2$Cl$_2$, 0.021 ml, 0,021 mmol) and a solution of triphenylphosphine (1.6 mg, 0.006 mmol) and tetrakis(triphenylphosphine) palladium (2.4 mg, 0.002 mmol) in 0.1 ml of methylene chloride. The reaction was stirred at room temperature for 30 min, during which time a pale yellow precipitate formed. The mixture was added dropwise to 2 ml of ice cold ethyl ether and the precipitate was collected by centrifugation, washing with ethyl ether. After drying, 7.6 mg of a pale yellow solid was obtained which was purified by reverse phase prep-TLC (1:6 CH$_3$CN:H$_2$O) to yield 4.2 mg (49%) of the title compound as a lyophilized solid.

$^1$H-NMR (300 MHz, 2:1 D$_2$O:CD$_3$CN): δ 1.65 (d, J=6.35 Hz, 3H, —CH$_3$), 3.52 (dd, J=9.58, 16.29 Hz, 1H, H1a), 3.82–3.93 (m, 2H, H1b, H6), 4.58–4.70 (m, 2H, H5, H8), 8.00–8.73 ppm (m, 6H, ArH).

UV (H$_2$O): λ$_{max}$=328 nm; ε=14,200.

IR (KBr): 1750 (β-lactam), 1670 (amide), 1600 cm$^{-1}$ (carboxylate).

EXAMPLE 29

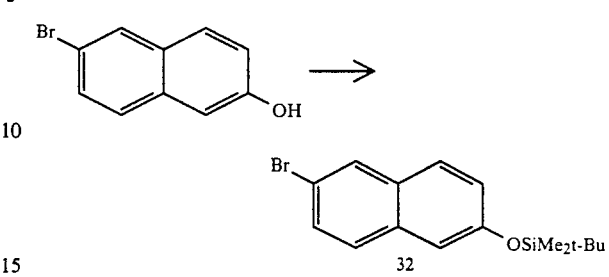

2-Bromo-6-(t-butyldimethylsilyloxy)-naphthalene (32)

To a solution of 6-bromo-2-naphthol (3.00 g, 13.5 mmol) in 67 ml of methylene chloride were added 4-dimethylaminopyridine (0.164 g, 1.34 mmol) and t-butyldimethylsilyl chloride (2.64 g, 17.5 mmol). The solution was cooled to 0° C. and triethylamine (2.60 ml, 18.7 mmol) was added. After 1.5 hours the reaction mixture was diluted with ethyl acetate and washed successively with saturated NH$_4$Cl, H$_2$O, and brine. Drying (MgSO$_4$), evaporation, and purification by flash chromatography through 130 g of silica gel (1:4 CH$_2$Cl$_2$/hexane) yielded 3.83 g (85%) of the title compound.

$^1$H-NMR (300 MHz, CDCl$_3$): δ 0.26 (s, 6H, SiMe$_2$), 1.04 (s, 9H, Sit-Bu), 7.11 (dd, J=7.9, 2.2 Hz, 1H), 7.17 (s, 1H), 7.49 (dd, J=8.8, 2.0 Hz, 1H), 7.57 (d, J=8.8 Hz, 1H), 7.64 (d, J=8.8 Hz, 1H), 7.93 ppm (s, 1H).

EXAMPLE 30

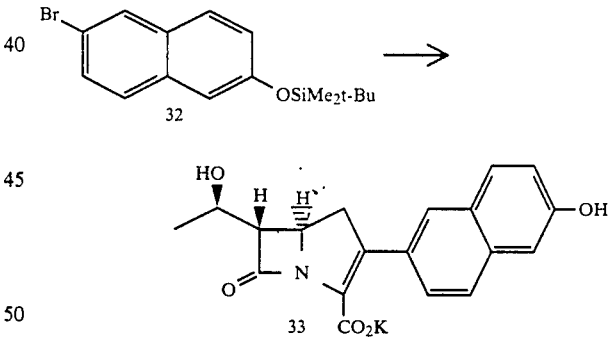

Potassium(5R,6S)-2-(2-hydroxy-6-naphthyl)-6-(1R-hydroxyethyl)-carbapen-2-em-3-carboxylate (33)

In a manner analogous to that described in Examples 3–5 and 12, but starting with 2-bromo-6-(t-butyldimethylsilyloxy)-naphthalene 32, the title compound was obtained as an off-white lyophilized solid.

$^1$H-NMR (300 MHz, D$_2$O): δ 1.34 (d, J=6.41 Hz, 3H, CH$_3$), 3.07 (dd, J=9.7, 16.9 Hz, 1H, H1a), 3.45 (dd, J=8.5, 16.9 Hz, 1H, H1b), 3.49 (dd, J=5.8, 2.8 Hz, 1H, H6), 4.20–4.35 (m, 2H, H8, H5), 7.16 (dd, J=8.9, 2.4 Hz, 1H), 7.22 (d, J=2.3 Hz, 1H), 7.45 (dd, J=8.6, 1.7 Hz, 1H), 7.67 (d, J=8.6 Hz, 1H), 7.70 (s, 1H), 7.78 ppm (d, J=8.9 Hz, 1H).

IR (KBr): 1745 (β-lactam), 1580 cm$^{-1}$ (carboxylate).
UV(H$_2$O): λ$_{max}$=318 nm, ε=14,800.

EXAMPLES 31-33

Operating as described in the preceding examples, the following compounds were analogously prepared:

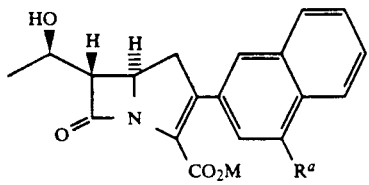

| EXAMPLE No. | $R^a$ | M | $\lambda_{max}$ (H$_2$O) |
|---|---|---|---|
| 31 | —CH$_2$N$_3$ | K | 283 nm |
| | | | 318 nm |
| 32 | ⟍=/—CN | K | 311 nm |
| 33 | /=/—CN | K | 310 nm |

What is claimed is:

1. A compound of the formula:

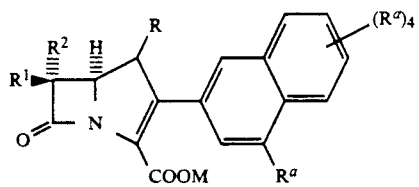

wherein:

R is H or CH$_3$;

$R^1$ and $R^2$ are independently H, CH$_3$—, CH$_3$CH$_2$—, (CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$—, or (CH$_3$)$_2$C(F)—;

$R^a$ are independently selected from the group consisting of hydrogen and the radicals set out below, provided that one to four $R^a$ radicals are other than hydrogen:

(a) a trifluoromethyl group: —CF$_3$;
(b) a halogen atom: —Br, —Cl, —F, or —I;
(c) C$_1$-C$_4$ alkoxy radical: —OC$_{1-4}$ alkyl, wherein the alkyl is optionally mono-substituted by $R^q$, where $R^q$ is a member selected from the group consisting of —OH, —OCH$_3$, —CN, —C(O)NH$_2$, —OC(O)NH$_2$, CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$, —COOM$^a$ (where M$^a$ is hydrogen, alkali metal, methyl or phenyl), tetrazolyl (where the point of attachment is the carbon atom of the tetrazole ring and one of the nitrogen atoms is mono-substituted by M$^a$ as defined above) and —SO$_3$M$^b$ (where M$^b$ is hydrogen or an alkali metal);

(d) a hydroxy group: —OH;
(e) a carbonyloxy radical: —O(C=O)R$^s$, where $R^s$ is C$_{1-4}$ alkyl or phenyl, each of which is optionally mono-substituted by $R^q$ as defined above;

(f) a carbamoyloxy radical: —O(C=O)N(R$^y$)R$^z$ where $R^y$ and $R^z$ are independently H, C$_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by —O—, —S— or —S(O)—, —S(O)$_2$—, to form a ring (where the ring is optionally mono-substituted with $R^q$ as defined above);

(g) a sulfur radical: —S(O)$_n$—R$^s$ where n=0-2, and R$^s$ is as defined above;

(h) a sulfamoyl group: —SO$_2$N(R$^y$)R$^z$ where R$^y$ and R$^z$ are as defined above;

(i) azido: N$_3$ (j) a formamido group: —N(R$^t$)(C=O)H, where R$^t$ is is H or C$_{1-4}$ alkyl, and the alkyl thereof is optionally mono-substituted by $R^q$ as defined above;

(k) a (C$_1$-C$_4$ alkyl)carbonylamino radical: —N(R$^t$)(C=O)C$_{1-4}$ alkyl, where R$^t$ is as defined above, and the alkyl group is also optionally mono-substituted by $R^q$ as defined above;

(l) a (C$_1$-C$_4$ alkoxy) carbonylamino radical: —N(R$^t$)(C=O)OC$_{1-4}$ alkyl, where R$^t$ is as defined above, and the alkyl group is also optionally mono-substituted by $R^q$ as defined above;

(m) a ureido group: —N(R$^t$)(C=O)N(R$^y$)R$^z$ where R$^t$, R$^y$ and R$^z$ are asdefined above;

(n) a sulfonamido group: —N(R$^t$)SO$_2$R$^s$, where R$^s$ and R$^t$ are as defined above;

(o) a cyano group: —CN;

(p) a formyl or acetalized formyl radical: —(C=O)H or —CH(OCH$_3$)$_2$;

(q) (C$_1$-C$_4$ alkyl)carbonyl radical wherein the carbonyl is acetalized: —C(OCH$_3$)$_2$C$_{1-4}$ alkyl, where the alkyl is optionally mono-substituted by $R^q$ as define above;

(r) carbonyl radical: —(C=O)R$^s$, where R$^s$ is as defined above;

(s) a hydroximinomethyl radical in which the oxygen or carbon atom is optionally substituted by a C$_1$-C$_4$ alkyl group: —(C=NOR$^z$)R$^y$ where R$^y$ and R$^z$ are as defined above, except they may not be joined together to form a ring;

(t) a (C$_1$-C$_4$ alkoxy)carbonyl radical: —(C=O)OC$_{1-4}$ alkyl, where the alkyl is optionally mono-substituted by $R^q$ as defined above;

(u) a carbomoyl radical: —(C=O)N(R$^y$)R$^z$ where R$^y$ and R$^z$ are as defined above;

(v) an N-hydroxycarbamoyl or N(C$_1$-C$_4$ alkoxy)-carbamoyl radical in which the nitrogen atom may be additionally substituted by a C$_1$-C$_4$ alkyl group: —(C=O)—N(OR$^y$)R$^z$ where R$^y$ and R$^z$ are as defined above, except they may not be joined together to form a ring;

(w) a thiocarbamoyl group: —(C=S)N(R$^y$)(R)$^z$ where R$^y$ and R$^z$ are as defined above;

(x) carboxyl: —COOM$^b$, where M$^b$ is as defined above;

(y) thiocyanate: —SCN;

(z) trifluoromethylthio: —SCF$_3$;

(aa) tetrazolyl, where the point of attachment is the carbon atom of the tetrazole ring and one of the nitrogen atoms is mono-substituted by hydrogen, an alkali metal or a C$_1$-C$_4$ alkyl optionally substituted by $R^q$ as defined above;

(ab) an anionic function selected from the group consisting of: phosphono [P=O(OM$^b$)$_2$]; alkylphosphono {P=O(OM$^b$)-[O(C$_1$-C$_4$ alkyl)]}; alkylphosphinyl [P=O(OM$^b$)-(C$_1$-C$_4$ alkyl)]; phosphoramido [P=O(OM$^b$)N(R$^y$)R$^z$ and P=O(OM$^b$)NHR$^x$]; sulfino (SO$_2$M$^b$); sulfo (SO$_3$M$^b$); acylsulfonamides selected from the structures CONM$^b$SO$_2$R$^x$, CONM$^b$SO$_2$N(R$^y$)R$^z$, SO$_2$NM$^b$CON(R$^y$)R$^z$; and SO$_2$NM$^b$CN, where R$^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by R$^q$, as defined above; M$^b$ is as defined above; and R$^y$ and R$^z$ are as defined above;

(ac) C$_5$-C$_7$ cycloalkyl group in which one of the carbon atoms in the ring is replaced by a heteroatom selected from O, S, NH or N(C$_1$-C$_4$ alkyl) and in which one additional carbon atom may be replaced by NH or N(C$_1$-C$_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

(ad) C$_2$-C$_4$ alkenyl radical, optionally mono-substituted by one of the substituents (a) to (ac) above and phenyl which is optionally substituted by R$^q$ as defined above;

(ae) C$_2$-C$_4$ alkynyl radical, optionally mono-substituted by one of the substituents (a) to (ac) above;

(af) C$_1$-C$_4$ alkyl radical;

(ag) C$_1$-C$_4$ alkyl mono-substituted by one of the substituents (a)-(ac) above;

(ah) a 2-oxazolidinonyl moiety in which the point of attachment is the nitrogen atom of the oxazolidinone ring, the ring oxygen atom is optionally replaced by a heteroatom selected from S and NR$^t$ (where R$^t$ is as defined above) and one of the saturated carbon atoms of the oxazolidinone ring is optionally mono-substituted by one of the substituents (a) to (ag) above;

M is selected from:
(i) hydrogen;
(ii) a pharmaceutically acceptable esterifying group or removable carboxyl protecting group;
(iii) an alkali metal or other pharmaceutically acceptable cation.

2. The compound of claim 1 wherein R$^1$ is hydrogen and R$^2$ is (R)—CH$_3$CH(OH)— or (R)—CH$_3$CH(F)—.

3. The compound of claim 1 wherein R$^a$ are independently selected from the group consisting of hydrogen and the radicals set out below, provided that one to four R$^a$ radicals are other than hydrogen:

| | |
|---|---|
| —OCH$_3$ | —OCH$_2$CO$_2$Na |
| —OCH$_2$CH$_2$OH | —CF$_3$ |
| —F | —Cl |
| —Br | —I |
| —OH | —OCOCH$_3$ |
| —OCONH$_2$ | —SCH$_3$ |
| —SOCH$_3$ | —SO$_2$CH$_3$ |
| —SCH$_2$CH$_2$OH | —SOCH$_2$CH$_2$OH |
| —SO$_2$NH$_2$ | —SO$_2$N(CH$_3$)$_2$ |
| —NHCHO | —NHCOCH$_3$ |
| —NHCO$_2$CH$_3$ | —NHSO$_2$CH$_3$ |
| —CN | —CHO |
| —COCH$_3$ | —COCH$_2$OH |
| —CH=NOH | —CH=NOCH$_3$ |
| —CH=NOCH$_2$CO$_2$H | —CH=NOCMe$_2$CO$_2$H |
| —CH=NOCMe$_2$CO$_2$Me | —CO$_2$CH$_2$CH$_2$OH |
| —CONH$_2$ | —CONHCH$_3$ |
| —CON(CH$_3$)$_2$ | —CONHCH$_2$CN |
| —CONHCH$_2$CONH$_2$ | —CONHCH$_2$CO$_2$H |
| —CONHOH | —CONHOCH$_3$ |
| -tetrazolyl | —CO$_2$Na |
| —SCF$_3$ | —PO$_3$NaH |
| —CONHSO$_2$Ph | —CONHSO$_2$NH$_2$ |
| —SO$_3$Na | —SO$_2$NHCN |
| —SO$_2$NHCONH$_2$ | —CH=CHCN |
| —CH=CHCONH$_2$ | —CH=CHCO$_2$Na |
| —C≡C—CONH$_2$ | —C≡C—CN |
| —CH$_2$OH | —CH$_2$N$_3$ |
| —CH$_2$CO$_2$Na | —SO$_2$CH$_2$CH$_2$OH and —CH$_2$I. |

4. A compound of the formula:

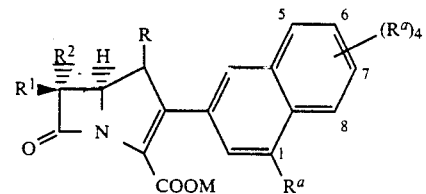

wherein R, R$^1$, R$^2$, R$^a$ (when it is not a hydrogen) and M are:

| # | R | R$^1$ | R$^2$ | M |
|---|---|---|---|---|
| 1 | —H | —H | —CH(F)CH$_3$ | K$^+$ |
| 2 | —H | —H | —CH(OH)CH$_3$ | K$^+$ |
| 3 | —H | —H | —CH(OH)CH$_3$ | K$^+$ |
| 4 | —H | —H | —CH(OH)CH$_3$ | K$^+$ |
| 5 | —H | —H | —CH(OH)CH$_3$ | K$^+$ |
| 6 | —H | —H | —CH(OH)CH$_3$ | K$^+$ |
| 7 | —H | —H | —CH(OH)CH$_3$ | K$^+$ |
| 8 | —H | —H | —CH(OH)CH$_3$ | —H |
| 9 | —H | —H | —CH(OH)CH$_3$ | Na$^+$ |
| 10 | —H | —H | —CH(OH)CH$_3$ | Na$^+$ |
| 11 | —H | —H | —CH(OH)CH$_3$ | —H |
| 12 | —H | —H | —CH(OH)CH$_3$ | K$^+$ |
| 13 | —H | —H | —CH(OH)CH$_3$ | Na$^+$ |
| 14 | —H | —H | —CH(OH)CH$_3$ | K$^+$ |
| 15 | —H | —H | —CH(OH)CH$_3$ | K$^+$ |
| 16 | —H | —H | —CH(OH)CH$_3$ | K$^+$ |
| 17 | —H | —H | —CH(OH)CH$_3$ | K$^+$ |
| 18 | —H | —H | —CH(F)CH$_3$ | K$^+$ |
| 19 | —H | —H | —CH(OH)CH$_3$ | Na$^+$ |
| 20 | —H | —H | —CH(OH)CH$_3$ | Na$^+$ |
| 21 | —H | —H | —CH(OH)CH$_3$ | K$^+$ |
| 22 | —H | —H | —CH(OH)CH$_3$ | K$^+$ |
| 23 | —H | —H | —CH(OH)CH$_3$ | Na$^+$ |
| 24 | —H | —H | —CH(OH)CH$_3$ | Na$^+$ |
| 25 | —H | —H | —CF$_2$CH$_3$ | K$^+$ |
| 26 | —CH$_3$ | —H | —CH(OH)CH$_3$ | K$^+$ |
| 27 | —H | —H | —CH(OH)CH$_3$ | K$^+$ |
| 28 | —H | —H | —CH(OH)CH$_3$ | K$^+$ |
| 29 | —H | —H | —CH(OH)CH$_3$ | K$^+$ |
| 30 | —H | —H | —CH(OH)CH$_3$ | K$^+$ |
| 31 | —H | —H | —CH(OH)CH$_3$ | Na$^+$ |
| 32 | —CH$_3$ | —H | —CH(OH)CH$_3$ | Na$^+$ |
| 33 | —H | —H | —CH(OH)CH$_3$ | —H |
| 34 | —H | —H | —CH(OH)CH$_3$ | K$^+$ |
| 35 | —H | —H | —CH(OH)CH$_3$ | K$^+$ |
| 36 | —H | —H | —CH(OH)CH$_3$ | K$^+$ |
| 37 | —H | —H | —CH(OH)CH$_3$ | K$^+$ |
| 38 | —H | —H | —CH(OH)CH$_3$ | K$^+$ |
| 39 | —H | —H | —CH(OH)CH$_3$ | K$^+$ |
| 40 | —H | —H | —CH(OH)CH$_3$ | K$^+$ |
| 41 | —H | —H | —CH(OH)CH$_3$ | Na$^+$ |

-continued

| # | R | R¹ | R² | M |
|---|---|---|---|---|
| 42 | —H | —H | —CH(OH)CH₃ | Na⁺ |
| 43 | —H | —H | —CH(OH)CH₃ | Na⁺ |
| 44 | —H | —H | —CH(OH)CH₃ | Na⁺ |
| 45 | —H | —H | —CH(OH)CH₃ | —H |
| 46 | —H | —H | —CH(OH)CH₃ | K⁺ |
| 47 | —H | —H | —CH(OH)CH₃ | K⁺ |
| 48 | —H | —H | —CH(OH)CH₃ | Na⁺ |
| 49 | —H | —H | —CH(OH)CH₃ | Na⁺ |
| 50 | —H | —H | —CH(F)CH₃ | Na⁺ |
| 51 | —H | —H | —CH(OH)CH₃ | K⁺ |
| 52 | —H | —H | —CH(OH)CH₃ | K⁺ |
| 53 | —H | —H | —CH(F)CH₃ | Na⁺ |
| 54 | —H | —H | —CH(OH)CH₃ | Na⁺ |
| 55 | —CH₃ | —H | —CH(OH)CH₃ | K⁺ |
| 56 | —H | —H | —CH₂CH₃ | K⁺ |
| 57 | —H | —H | —CH(OH)CH₃ | Na⁺ |
| 58 | —H | —H | —CH₂CH₃ | K⁺ |
| 59 | —H | —H | —CH(OH)CH₃ | K⁺ |
| 60 | —H | —H | —CH(OH)CH₃ | K⁺ |
| 61 | —H | —H | —CH(OH)CH₃ | K⁺ |
| 62 | —H | —H | —CH(OH)CH₃ | K⁺ |
| 63 | —H | —H | —CH(OH)CH₃ | K⁺ |
| 64 | —H | —H | —CH(OH)CH₃ | K⁺ |
| 65 | —H | —H | —CH(OH)CH₃ | K⁺ |
| 66 | —H | —H | —CH(OH)CH₃ | K⁺ |
| 67 | —H | —H | —CH(OH)CH₃ | K⁺ |
| 68 | —H | —H | —CH(OH)CH₃ | K⁺ |
| 69 | —H | —H | —CH(OH)CH₃ | K⁺ |
| 70 | —OH | —H | —CH(OH)CH₃ | K⁺ |
| 71 | —H | —H | —CH(OH)CH₃ | K⁺ |
| 72 | —H | —H | —CH(F)CH₃ | K⁺ |
| 73 | —H | —H | —CH(OH)CH₃ | K⁺ |
| 74 | —H | —H | —CH(F)CH₃ | Na⁺ |
| 75 | —H | —H | —CH(OH)CH₃ | Na⁺ |
| 76 | —H | —H | —CH(OH)CH₃ | Na⁺ |
| 77 | —H | —H | —CH(F)CH₃ | Na⁺ |
| 78 | —H | —H | —CH₂OH | Na⁺ |
| 79 | —H | —H | —CH(OH)CH₃ | K⁺ |
| 80 | —H | —H | —CH(OH)CH₃ | K⁺ |
| 81 | —H | —H | —CH(OH)CH₃ | K⁺ |
| 82 | —H | —H | —CH(OH)CH₃ | K⁺ |
| 83 | —H | —H | —CH(OH)CH₃ | K⁺ |
| 84 | —H | —H | —CH(OH)CH₃ | K⁺ |
| 85 | —H | —H | —CH(OH)CH₃ | K⁺ |
| 86 | —H | —H | —CH(OH)CH₃ | K⁺ |
| 87 | —H | —H | —CH(OH)CH₃ | K⁺ |
| 88 | —H | —H | —CH(OH)CH₃ | K⁺ |
| 89 | —H | —H | —CH(OH)CH₃ | K⁺ |
| 90 | —H | —H | —CH(OH)CH₃ | K⁺ |
| 91 | —H | —H | —CH(OH)CH₃ | K⁺ |
| 92 | —H | —H | —CH(OH)CH₃ | K⁺ |

| # | Rᵃ | Ra position |
|---|---|---|
| 1 | —CN | 1 |
| 2 | —CN | 5 |
| 3 | —CN | 6 |
| 4 | —CN | 7 |
| 5 | —CN | 8 |
| 6 | —OCH₃ | 8 |
| 7 | —OCH₂CO₂Na | 1 |
| 8 | —OCH₂CH₂OH | 7 |
| 9 | —CF₃ | 1 |
| 10 | —F | 1 |
| 11 | —Cl | 6 |
| 12 | —Br | 7 |
| 13 | —F | 1,6,7,8 |
| 14 | —OH | 6,7 |
| 15 | —OCOCH₃ | 7 |
| 16 | —OCONH₂ | 1 |
| 17 | —SCH₃ | 1 |
| 18 | —SOCH₃ | 7 |
| 19 | —SO₂CH₃ | 1 |
| 20 | —SCH₂CH₂OH | 1 |
| 21 | —SOCH₂CH₂OH | 6 |
| 22 | —SCH₂CONH₂ | 1 |
| 23 | —SO₂NH₂ | 1 |
| 24 | —SO₂N(CH₃)₂ | 1,5 |
| 25 | —NHCHO | 6,8 |
| 26 | —NHCOCH₃ | 6,8 |
| 27 | —NHCO₂CH₃ | 1,6 |
| 28 | —NHSO₂CH₃ | 1 |
| 29 | —COCH₃ | 1 |
| 30 | —COCH₂OH | 6 |
| 31 | —CH=NOCH₃ | 6 |
| 32 | —CH=NOCH₂CO₂Na | 7 |
| 33 | —CH=NOCMe₂CO₂H | 1 |
| 34 | —CH=NOCMe₂CO₂Me | 8 |
| 35 | —CO₂CH₂CH₂OH | 1 |
| 36 | —CONHCH₃ | 8 |
| 37 | —CON(CH₃)₂ | 6 |
| 38 | —CONHCH₂CN | 1 |
| 39 | —CONHCH₂CONH₂ | 1 |
| 40 | —CONHCH₂CO₂H | 6 |
| 41 | —CONHOH | 1 |
| 42 | —CONHOCH₃ | 7 |
| 43 | -tetrazolyl | 1 |
| 44 | —SCF₃ | 1 |
| 45 | —PO₃NaH | 7 |
| 46 | —CONHSO₂Ph | 7 |
| 47 | —CONHSO₂NH₂ | 1 |
| 48 | —SO₃Na | 7 |
| 49 | —SO₂NHCN | 1 |
| 50 | —SO₂NHCONH₂ | 1 |
| 51 | —CH=CHCN | 8 |
| 52 | —CH=CHCONH₂ | 1 |
| 53 | —CH=CHCO₂Na | 7 |
| 54 | —C≡C—CONH₂ | 1 |
| 55 | —C≡C—CN | 1 |
| 56 | —CH₂N₃ | 8 |
| 57 | —CH₂CO₂Na | 7 |
| 58 | —OH | 3 |
| 59 | —CHO | 1 |
| 60 | —CHO | 5 |
| 61 | —CHO | 6 |
| 62 | —CHO | 7 |
| 63 | —CHO | 8 |
| 64 | —CH=NOH | 1 |
| 65 | —CH=NOH | 5 |
| 66 | —CH=NOH | 6 |
| 67 | —CH=NOH | 7 |
| 68 | —CH=NOH | 8 |
| 69 | —CONH₂ | 1 |
| 70 | —CONH₂ | 5 |
| 71 | —CONH₂ | 6 |
| 72 | —CONH₂ | 7 |
| 73 | —CONH₂ | 8 |
| 74 | —CO₂Na | 1 |
| 75 | —CO₂Na | 5 |
| 76 | —CO₂Na | 6 |
| 77 | —CO₂Na | 7 |
| 78 | —CO₂Na | 8 |
| 79 | —CH₂OH | 8 |
| 80 | —CH₂OH | 5 |
| 81 | —CH₂OH | 6 |
| 82 | —CH₂OH | 7 |
| 83 | —CH₂N₃ | 1 |
| 84 | —CH₂OCONH₂ | 1 |
| 85 | —CN | 1 |
| 86 | —(Z)—CH=CHCN | 1 |
| 87 | —(E)—CH=CHCN | 1 |
| 88 | —CH₂OH | 1 |
| 89 | —CONH₂ | 7 |
| 90 | —OH | 7 |
| 91 | —(Z)—CH=CHCN | 7 |
| 92 | —(E)—CH=CHCN | 7 |

| # | R | R¹ | R² | M |
|---|---|---|---|---|
| 93 | —H | —H | —CH(OH)CH₃ | K⁺ |
| 94 | —H | —H | —CH(OH)CH₃ | K⁺ |
| 95 | —H | —H | —CH(OH)CH₃ | K⁺ |
| 96 | —H | —H | —CH(OH)CH₃ | K⁺ |
| 97 | —H | —H | —CH(OH)CH₃ | K⁺ |
| 98 | —H | —H | —CH(OH)CH₃ | K⁺ |
| 99 | —H | —H | —CH(OH)CH₃ | K⁺ |
| 100 | —H | —H | —CH(OH)CH₃ | K⁺ |
| 101 | —H | —H | —CH(OH)CH₃ | K⁺ |
| 102 | —H | —H | —CH(OH)CH₃ | K⁺ |
| 103 | —H | —H | —CH(OH)CH₃ | K⁺ |
| 104 | —H | —H | —CH(OH)CH₃ | K⁺ |

| # | Rᵃ | Ra' |
|---|---|---|
| 93 | 1-F | 7-CH₂OH |
| 94 | 1-F | 7-CHO |
| 95 | 1-F | 7-CONH₂ |

| | -continued | |
|---|---|---|
| 96 | 1-SOCH₃ | 7-CHO |
| 97 | 1-SOCH₃ | 8-CHO |
| 98 | 1-CN | 7-SOCH₃ |
| 99 | 1-CONH₂ | 7-CH₂OH |
| 100 | 1-CONH₂ | 8-SOCH₃ |
| 101 | 1-CN | 8-CH₂OH |
| 102 | 7-CHO | 8-OH |
| 103 | 1-CONH₂ | 7-CHO or |
| 104 | 1-CN | 7-CO₂K. |

5. A pharmaceutical composition for antibacterial use comprising an antibacterially effective amount of a compound of claim 1 and a pharmaceutically acceptable carrier therefor.

6. A method of treating bacterial infections in human or animal subjects in need of such treatment comprising administering to such subject an antibacterially effective amount of a compound of claim 1.

7. A pharmaceutical composition for antibacterial use comprising an antibacterially effective amount of a compound of claim 1, an inhibitorily effective amount of a DHP inhibitor, and, optionally, a pharmaceutically acceptable carrier therefor.

8. The pharmaceutical composition according to claim 9 wherein the DHP inhibitor is 7-(L-2-amino-2-carboxyethylthio)-2-(2,2-dimethylcyclopropanecarboxamide)-2-heptenoic acid.

9. A method of treating bacterial infections in human or animal subjects in need of such treatment comprising coadministering to such subject an antibacterially effective amount of a compound of claim 1 and an inhibitorily effective amount of a DHP inhibitor.

10. The method according to claim 11 wherein the DHP inhibitor is 7-(L-2-amino-2-carboxyethylthio)-2-(2,2-dimethylcyclopropanecarboxamide)-2-heptenoic acid.

* * * * *